(12) United States Patent
Colborn et al.

(10) Patent No.: US 7,541,489 B2
(45) Date of Patent: *Jun. 2, 2009

(54) METHOD OF MAKING HALOPHTHALIC ACIDS AND HALOPHTHALIC ANHYDRIDES

(75) Inventors: Robert Edgar Colborn, Niskayuna, NY (US); David Bruce Hall, Ballston Lake, NY (US); Peter Alois Koch, Frankfurt (DE); Bernd Volker Demuth, Offenbach (DE); Thomas Wessel, Niederdorfelden (DE); KarlErnst Mack, Wiesbaden (DE); Prashant Anil Tatake, Mumbai (IN); Utpal Mahendra Vakil, Mumbai (IN); Shyamal Bhaskar Gondkar, Bangalore (IN); John Edward Pace, Washington, WV (US); Kwang Woong Won, San Clemente, CA (US)

(73) Assignee: SABIC Innovative Plastics IP B.V., Bergen op Zoom (NL)

( * ) Notice: Subject to any disclaimer, the term of this patent is extended or adjusted under 35 U.S.C. 154(b) by 214 days.

This patent is subject to a terminal disclaimer.

(21) Appl. No.: 11/170,708

(22) Filed: Jun. 29, 2005

(65) Prior Publication Data
US 2006/0004224 A1 Jan. 5, 2006

Related U.S. Application Data

(63) Continuation-in-part of application No. 10/882,762, filed on Jun. 30, 2004, now abandoned.

(51) Int. Cl.
*C07C 51/16* (2006.01)
(52) U.S. Cl. .................. 562/416; 548/476; 549/246
(58) Field of Classification Search ................ 562/416; 548/476; 549/246
See application file for complete search history.

(56) References Cited

U.S. PATENT DOCUMENTS 2,245,528 A 6/1941 Loder .................. 260/524

(Continued)

FOREIGN PATENT DOCUMENTS

EP 0 066 436 5/1982

(Continued)

OTHER PUBLICATIONS

Chervinakil et al. "Kinetics of the Oxidation of Chloro and Nitro-o-Xylenes With Molecular Oxygen", Russian Journal of Physical Chemistry, vol. 43, No. 8, pp. 1154-1157, 1969.

(Continued)

*Primary Examiner*—Jafar Parsa
*Assistant Examiner*—Chukwuma O Nwaonicha

(57) ABSTRACT

A method of preparing a halophthalic acid is disclosed which comprises the steps of contacting in a liquid phase reaction mixture at least one halogen-substituted ortho-xylene with oxygen and acetic acid at a temperature in a range between about 120° C. and about 220° C. in the presence of a catalyst system yielding a product mixture comprising less than 10 percent halogen-substituted ortho-xylene starting material, a halophthalic acid product, and less than about 10,000 ppm halobenzoic acid and less than about 1000 ppm halophthalide by-products based on a total amount of halophthalic acid present in the product mixture. In addition methods for the preparation of halophthalic anhydride, and recovery of high purity acetic acid from an aqueous acetic acid stream comprising HCl, which is generated during the preparation of the halophthalic acid are also disclosed.

30 Claims, 3 Drawing Sheets

Fig. 3

U.S. PATENT DOCUMENTS

| | | | |
|---|---|---|---|
| 2,415,800 A | 2/1947 | Rust | 260/524 |
| 2,445,528 A | 7/1948 | Keogh, Jr. | 30/41 |
| 2,833,816 A | 5/1958 | Saffer et al. | 260/524 |
| 2,883,816 A | 4/1959 | Kroll | 53/244 |
| 2,925,425 A | 2/1960 | Contois, Jr. et al. | 260/346.4 |
| 2,930,802 A | 3/1960 | Aries | 260/346.4 |
| 3,012,038 A | 12/1961 | O'Neill et al. | 260/295 |
| 3,086,991 A | 4/1963 | Keith et al. | 260/524 |
| 3,089,906 A | 5/1963 | Saffer et al. | 260/524 |
| 3,089,907 A | 5/1963 | Saffer et al. | 260/524 |
| 3,092,658 A | 6/1963 | Baldwin et al. | 260/524 |
| 3,161,658 A | 12/1964 | Meyer | 260/346.3 |
| 3,176,039 A | 3/1965 | Hay | 260/488 |
| 3,299,125 A | 1/1967 | Ichikawa | 260/524 |
| 3,334,135 A | 8/1967 | Ichikawa | 260/524 |
| 3,357,994 A | 12/1967 | Popp et al. | 260/327 |
| 3,402,184 A | 9/1968 | Berthoux et al. | 260/346.4 |
| 3,442,954 A | 5/1969 | Crocker et al. | 260/592 |
| 3,484,458 A | 12/1969 | Stein et al. | 260/346.4 |
| 3,549,695 A | 12/1970 | Bryant, Jr. et al. | 260/525 |
| 3,557,173 A | 1/1971 | Trevillyan | 260/439 |
| 3,578,706 A | 5/1971 | List et al. | 260/524 |
| 3,626,001 A | 12/1971 | Keith et al. | 260/574 |
| 3,655,521 A | 4/1972 | Gehrken et al. | 203/28 |
| 3,660,476 A | 5/1972 | Ichikawa et al. | 260/524 |
| 3,673,154 A | 6/1972 | Trevillyan | 260/524 |
| 3,681,399 A | 8/1972 | Barth | 260/346.4 |
| 3,721,708 A | 3/1973 | List et al. | 260/524 |
| 3,781,344 A | 12/1973 | Celle-St.-Cloud et al. | 260/524 |
| 3,839,436 A | 10/1974 | Longland, Jr. | 260/524 |
| 3,862,145 A | 1/1975 | Brennan et al. | 260/346.4 |
| 3,865,870 A | 2/1975 | Cronauer et al. | 260/524 |
| 3,865,871 A | 2/1975 | Horie et al. | 260/524 |
| 3,919,306 A | 11/1975 | Johnson et al. | 260/524 |
| 3,920,735 A | 11/1975 | Wampfler et al. | 260/524 |
| 3,950,409 A | 4/1976 | Yokota et al. | 260/524 |
| 3,970,696 A | 7/1976 | Shigeyasu et al. | 260/524 |
| 3,996,271 A | 12/1976 | Yokota et al. | 260/524 |
| 4,051,178 A | 9/1977 | Kimura et al. | 260/524 |
| 4,053,506 A | 10/1977 | Park et al. | 260/525 |
| 4,081,464 A | 3/1978 | Marsh et al. | 260/524 |
| 4,131,742 A | 12/1978 | Hudson | 560/241 |
| 4,141,909 A | 2/1979 | Wiedemann et al. | 260/346.4 |
| 4,145,560 A | 3/1979 | Alagy et al. | 562/412 |
| 4,150,151 A | 4/1979 | Pader et al. | 424/56 |
| 4,165,324 A | 8/1979 | Schroeder et al. | 260/346.7 |
| 4,172,209 A | 10/1979 | Vora | 562/414 |
| 4,211,881 A | 7/1980 | Horsfield et al. | 562/416 |
| 4,211,882 A | 7/1980 | Komatsu et al. | 562/416 |
| 4,215,051 A | 7/1980 | Schroeder et al. | 260/346.7 |
| 4,215,052 A | 7/1980 | Schroeder et al. | 260/346.7 |
| 4,215,053 A | 7/1980 | Palmer et al. | 260/346.7 |
| 4,215,054 A | 7/1980 | Schroeder et al. | 260/346.7 |
| 4,215,055 A | 7/1980 | Palmer et al. | 260/346.7 |
| 4,215,056 A | 7/1980 | Schroeder et al. | 260/346.7 |
| 4,233,227 A | 11/1980 | Schroeder et al. | 260/346.7 |
| 4,234,494 A | 11/1980 | Schroeder et al. | 260/346.7 |
| 4,241,220 A | 12/1980 | Itaya et al. | 562/414 |
| 4,243,636 A | 1/1981 | Shiraki et al. | 422/225 |
| 4,250,330 A | 2/1981 | Costantini et al. | 562/409 |
| 4,278,810 A | 7/1981 | Hanotier | 562/412 |
| 4,284,523 A | 8/1981 | Darin et al. | 252/420 |
| 4,297,283 A | 10/1981 | Verbicky | 260/346.3 |
| 4,299,977 A | 11/1981 | Kuhlmann et al. | 562/416 |
| 4,314,073 A | 2/1982 | Crooks | 562/416 |
| 4,322,549 A | 3/1982 | Kuhlmann et al. | 562/416 |
| 4,329,493 A | 5/1982 | Hashizume et al. | 562/414 |
| 4,334,086 A | 6/1982 | Hanotier et al. | 562/413 |
| 4,339,599 A | 7/1982 | Jongsma | 562/412 |
| 4,370,487 A | 1/1983 | Meyer et al. | 549/242 |
| 4,387,243 A | 6/1983 | Naim et al. | 562/413 |
| 4,389,334 A | 6/1983 | Weinert, Jr. et al. | 252/429 |
| 4,436,922 A | 3/1984 | Kita et al. | 549/251 |
| 4,447,646 A | 5/1984 | Johnson et al. | 562/487 |
| 4,459,365 A | 7/1984 | Suzuki et al. | 502/24 |
| 4,469,878 A | 9/1984 | Kaneyasu et al. | 549/248 |
| 4,477,380 A | 10/1984 | Knips et al. | 260/385 |
| 4,481,304 A | 11/1984 | Sato et al. | 502/209 |
| 4,489,204 A | 12/1984 | Neri et al. | 549/248 |
| 4,582,912 A | 4/1986 | Saleh et al. | 549/239 |
| 4,587,350 A | 5/1986 | Kilner et al. | 549/245 |
| 4,593,122 A | 6/1986 | Hashizume et al. | 562/414 |
| 4,594,449 A | 6/1986 | Takuma et al. | 562/416 |
| 4,603,220 A | 7/1986 | Feld | 562/416 |
| 4,605,757 A | 8/1986 | Feld | 562/416 |
| 4,632,998 A | 12/1986 | Geissen et al. | 549/248 |
| 4,675,420 A | 6/1987 | Block et al. | 549/248 |
| 4,677,240 A | 6/1987 | Carlson et al. | 585/488 |
| 4,725,570 A | 2/1988 | Sikkenga et al. | 502/204 |
| 4,755,622 A | 7/1988 | Schammel et al. | 562/413 |
| 4,769,487 A | 9/1988 | Hundley et al. | 562/413 |
| 4,769,489 A | 9/1988 | Abrams et al. | 562/416 |
| 4,777,287 A | 10/1988 | Zeitlin et al. | 562/414 |
| 4,785,121 A | 11/1988 | Leone-Bay et al. | 549/246 |
| 4,786,753 A | 11/1988 | Partenheimer et al. | 562/416 |
| 4,792,621 A | 12/1988 | Abrams | 562/414 |
| 4,816,601 A | 3/1989 | Lowry et al. | 562/413 |
| 4,827,025 A | 5/1989 | Shiraki et al. | 562/414 |
| 4,830,789 A | 5/1989 | Hinenoya et al. | 660/546 |
| 4,845,241 A | 7/1989 | Edwards et al. | 549/260 |
| 4,845,274 A | 7/1989 | Schammel et al. | 562/413 |
| 4,855,491 A | 8/1989 | Chew et al. | 562/414 |
| 4,855,492 A | 8/1989 | Hundley | 562/414 |
| 4,876,386 A | 10/1989 | Holzhauer et al. | 562/414 |
| 4,877,900 A | 10/1989 | Tamaru et al. | 562/413 |
| 4,879,387 A | 11/1989 | Hara | 549/248 |
| 4,895,978 A | 1/1990 | Darin et al. | 562/416 |
| 4,900,480 A | 2/1990 | Litz et al. | 261/36.1 |
| 4,900,865 A | 2/1990 | Hussmann et al. | 562/412 |
| 4,906,771 A | 3/1990 | Young et al. | 562/416 |
| 4,908,471 A | 3/1990 | Leuck et al. | 560/77 |
| 4,910,175 A | 3/1990 | Michel et al. | 502/24 |
| 4,939,297 A | 7/1990 | Browder et al. | 562/485 |
| 4,950,786 A | 8/1990 | Sanchez et al. | 562/416 |
| 4,952,721 A | 8/1990 | Fjare | 560/131 |
| 4,978,760 A | 12/1990 | Spohn | 549/246 |
| 4,992,579 A | 2/1991 | Schammel | 562/413 |
| 4,992,580 A | 2/1991 | Partenheimer | 562/416 |
| 4,996,353 A | 2/1991 | Lee et al. | 562/412 |
| 5,003,088 A | 3/1991 | Spohn et al. | 549/246 |
| 5,004,830 A | 4/1991 | Park et al. | 562/413 |
| 5,028,737 A | 7/1991 | Sanchez | 562/416 |
| 5,041,633 A | 8/1991 | Partenheimer et al. | 562/413 |
| 5,049,682 A | 9/1991 | Tang et al. | 549/246 |
| 5,055,612 A | 10/1991 | Tachibana et al. | 562/416 |
| 5,059,697 A | 10/1991 | Fertel et al. | 549/246 |
| 5,081,290 A | 1/1992 | Partenheimer et al. | 562/416 |
| 5,082,959 A | 1/1992 | Ernst et al. | 556/438 |
| 5,087,741 A | 2/1992 | Tennant et al. | 562/414 |
| 5,095,141 A | 3/1992 | Schammel et al. | 562/414 |
| 5,095,142 A | 3/1992 | Janulis | 562/414 |
| 5,095,143 A | 3/1992 | Heberer et al. | 562/416 |
| 5,095,146 A | 3/1992 | Zeitlin et al. | 562/486 |
| 5,099,064 A | 3/1992 | Huber, Jr. et al. | 562/414 |
| 5,112,992 A | 5/1992 | Belmonte et al. | 549/245 |
| 5,132,450 A | 7/1992 | Tanaka et al. | 562/414 |
| 5,169,820 A | 12/1992 | Ueda et al. | 502/209 |
| 5,183,933 A | 2/1993 | Harper et al. | 562/414 |
| 5,185,451 A | 2/1993 | Stults et al. | 548/418 |
| 5,206,391 A | 4/1993 | Seper et al. | 549/246 |
| 5,210,223 A | 5/1993 | Chen et al. | 549/247 |
| 5,225,573 A | 7/1993 | Shorr et al. | 549/246 |
| 5,225,574 A | 7/1993 | Aichinger et al. | 549/248 |
| 5,225,575 A | 7/1993 | Ivanov et al. | 549/249 |

| | | | |
|---|---|---|---|
| 5,229,482 A | 7/1993 | Brunelle | 528/125 |
| 5,229,527 A | 7/1993 | Ueda et al. | 549/248 |
| 5,233,054 A | 8/1993 | Tang et al. | 549/246 |
| 5,235,071 A | 8/1993 | Ueda et al. | 549/248 |
| 5,242,643 A | 9/1993 | Kim et al. | 422/129 |
| 5,250,724 A | 10/1993 | Fumagalli et al. | 562/416 |
| 5,264,588 A | 11/1993 | Krishnan | 548/476 |
| 5,300,201 A | 4/1994 | Seper et al. | 204/157.6 |
| 5,322,954 A | 6/1994 | Seper et al. | 549/246 |
| 5,324,702 A | 6/1994 | Yoo et al. | 502/204 |
| 5,332,707 A | 7/1994 | Karayannis et al. | 502/113 |
| 5,334,754 A | 8/1994 | Sumner, Jr. et al. | |
| 5,342,968 A | 8/1994 | Brugge et al. | |
| 5,359,133 A | 10/1994 | Nazimok et al. | |
| 5,371,283 A | 12/1994 | Kingsley et al. | |
| 5,453,538 A | 9/1995 | Broeker et al. | 562/409 |
| 5,473,101 A | 12/1995 | Johnstone et al. | 562/416 |
| 5,510,521 A | 4/1996 | McGehee et al. | 562/414 |
| 5,557,009 A | 9/1996 | Izumisawa et al. | 562/412 |
| 5,574,172 A | 11/1996 | Katsuro et al. | 549/246 |
| 5,596,129 A | 1/1997 | Murashige et al. | 562/414 |
| 5,612,007 A | 3/1997 | Abrams | 422/189 |
| 5,637,764 A | 6/1997 | Rohrscheid et al. | 562/416 |
| 5,679,847 A | 10/1997 | Ohkoshi et al. | 562/416 |
| 5,683,553 A | 11/1997 | Baur et al. | 203/1 |
| 5,693,856 A | 12/1997 | Ramachandran et al. | 562/414 |
| 5,696,285 A | 12/1997 | Roby | 562/416 |
| 5,705,682 A | 1/1998 | Ohkoshi et al. | 562/414 |
| 5,723,656 A | 3/1998 | Abrams | 562/412 |
| 5,739,384 A | 4/1998 | Albillos et al. | 562/414 |
| 5,763,648 A | 6/1998 | Hashizume et al. | 562/414 |
| 5,763,649 A | 6/1998 | Fukuhara | 562/416 |
| 5,830,974 A | 11/1998 | Schmidhauser et al. | 528/125 |
| 5,880,313 A | 3/1999 | Zaima et al. | 562/414 |
| 5,919,977 A | 7/1999 | Murakami et al. | 562/412 |
| 5,925,786 A | 7/1999 | Isayama et al. | 562/412 |
| 5,958,821 A | 9/1999 | Ishii et al. | 502/167 |
| 5,959,140 A | 9/1999 | Okoshi et al. | 562/414 |
| 5,961,942 A | 10/1999 | Turner et al. | 423/240 |
| 5,969,164 A | 10/1999 | Budge et al. | 549/508 |
| 5,981,420 A | 11/1999 | Nakano et al. | 502/155 |
| 6,018,077 A | 1/2000 | Ohkoshi et al. | 562/414 |
| 6,020,522 A | 2/2000 | Ishii et al. | 562/410 |
| 6,034,269 A | 3/2000 | Turner et al. | 562/412 |
| 6,114,574 A | 9/2000 | Sen et al. | 562/410 |
| 6,114,575 A | 9/2000 | McMahon et al. | 562/414 |
| 6,133,476 A | 10/2000 | Lin | 562/486 |
| 6,150,553 A | 11/2000 | Parten | 560/248 |
| 6,153,790 A | 11/2000 | June et al. | 562/414 |
| 6,160,170 A | 12/2000 | Codignola | 562/413 |
| 6,175,038 B1 | 1/2001 | Jhung et al. | 562/412 |
| 6,180,822 B1 | 1/2001 | Jhung et al. | 562/412 |
| 6,355,835 B1 | 3/2002 | Kulsrestha et al. | 562/417 |
| 6,380,399 B1 | 4/2002 | Okuno et al. | 549/250 |
| 6,649,773 B2 * | 11/2003 | Colborn et al. | 548/476 |
| 6,657,067 B2 * | 12/2003 | Colborn et al. | 548/476 |
| 6,657,068 B2 * | 12/2003 | Colborn et al. | 548/476 |
| 6,670,487 B1 | 12/2003 | Colborn et al. | |

FOREIGN PATENT DOCUMENTS

| | | |
|---|---|---|
| EP | 0 087 678 | 2/1983 |
| EP | 0 099 078 | 7/1983 |
| EP | 0 135 341 | 8/1984 |
| EP | 0 137 548 | 9/1984 |
| EP | 0 077 334 | 11/1984 |
| EP | 0 256 352 | 7/1987 |
| EP | 0 257 788 A1 | 7/1987 |
| EP | 0 257 788 B1 | 7/1987 |
| EP | 0 261 892 | 9/1987 |
| EP | 0 279 288 | 2/1988 |
| EP | 0 318 205 | 11/1988 |
| EP | 0 375 812 | 12/1988 |
| EP | 0 330 219 | 2/1989 |
| EP | 0 334 049 | 2/1989 |
| EP | 0 338 215 | 2/1989 |
| EP | 0 341 813 | 3/1989 |
| EP | 0 343 991 | 5/1989 |
| EP | 0 361 798 | 9/1989 |
| EP | 0 417 691 | 9/1990 |
| EP | 0 440 593 | 1/1991 |
| EP | 0 639 174 | 11/1991 |
| EP | 0 593 546 | 6/1992 |
| EP | 0 641 303 | 5/1993 |
| EP | 0 601 177 | 6/1993 |
| EP | 0 673 910 | 3/1995 |
| EP | 0 682 000 | 5/1995 |
| EP | 0 682 005 | 5/1995 |
| EP | 0 734 372 | 9/1995 |
| EP | 0 713 856 | 11/1995 |
| EP | 0 719 754 | 12/1995 |
| EP | 0 764 626 | 9/1996 |
| EP | 0 781 754 | 12/1996 |
| EP | 0 796 837 | 3/1997 |
| EP | 0 818 433 | 7/1997 |
| EP | 0 889 021 | 10/1997 |
| EP | 0 860 423 | 2/1998 |
| EP | 0 962 442 | 6/1999 |
| WO | WO 95/09143 | 4/1995 |
| WO | WO 96/30327 | 10/1996 |
| WO | WO 96/31455 | 10/1996 |
| WO | WO 96/40610 | 12/1996 |
| WO | WO 97/27168 | 7/1997 |
| WO | WO 97/36673 | 10/1997 |
| WO | WO 99/05086 | 2/1999 |
| WO | WO 99/14178 | 3/1999 |
| WO | WO 99/14179 | 3/1999 |
| WO | WO 99/31038 | 6/1999 |
| WO | WO 99/37599 | 7/1999 |
| WO | WO 99/42430 | 8/1999 |
| WO | WO 99/54274 | 10/1999 |
| WO | WO 99/59953 | 11/1999 |
| WO | WO 00/37406 | 6/2000 |
| WO | WO 00/37407 | 6/2000 |
| WO | WO 0063146 | 10/2000 |
| WO | WO 00/66529 | 11/2000 |
| WO | WO 01/14308 | 3/2001 |
| WO | WO 01/38282 | 5/2001 |
| WO | WO 01/92195 | 12/2001 |
| WO | WO 02/30861 | 4/2002 |
| WO | WO 03/082791 | 10/2003 |

OTHER PUBLICATIONS

Nazarenko et al., "Production of Monochlorophthalic Acids By Liquid Phase Catalytic Oxidation of Chloro-oXylenes", Ukrainskly Khimicheskly Zhurnal, vol. 50, No. 6, pp. 644-647, 1984.

Greene et al., "The Journal of Organic Chemistry", vol. 38, No. 6, pp. 1242-1245, Mar. 23, 1973.

Partenheimer, "Thermodynamic and Kinetic Studies to Elucidate the Amoco Co/Mn/Br. Autoxidation ("MC") Catalyst", Act. Dioxygen Homogeneous Catal. Oxid., 5th, pp. 474, 1993, (Abstract).

Gipe et al., "Catalysts By Rational Design: Prediction and Confirmation of the Properties of the Co/Ce/Br Liquid-Phase Autoxidation Catalyst Based on the Kinetic Similarity to the Co/Mn/Br Catalyst", Stud. Surf. Sci. Catal., pp. 1117-1127, 1997, (Abstract).

Kulakov et al, "Study of the Mechanism of the Oxidation of Aromatic Hydrocarbons and Development of Technology of Synthesis of Terephthalic Acid", Mendeleevsk, S'ezd Obshch. Prikl. Khim., vol. 11, pp. 323-324, 1975, (Abstrract).

Partenheimer, "Novel Catalytic Characteristics of the Co/Mn/Cl/Br Liquid Phase Oxidation Catalyst (1)", Chem. Ind., pp. 357-368, 1998, (Abstract).

Bhatia et al., "Colbalt (II)-Catalyzed Reaction of Aldehydes With Acetic Anhydride Under an Oxygen Atmosphere: Scope and Mechanism", J. Org. Chem., vol. 58, No. 20, pp. 5518-5523, 1993, (Abstract).

Uzuiniece et al., "Liquid-Phase Catalytic oxidation of 4-bromo-o-xylene", Chemical Abstracts + Indexes, American Chemical Society, vol. 90, No. 5, 1979, XP002165078 (Abstract ).

Clark et al., "Catalytic Oxidation of the Side Chain of Alkylaromatics Using a Triphasic System", Synthetic Communications, vol. 30, No. 20, pp. 3731-3735, 2000.

Serija et al.., "Study of the Effect of a Substituent on the Process of Liquid Phase Catalytic Oxidation of 4-Substituted o-Xylenes", Riga Polytechnic Institute, pp. 72-72, Sep. 4, 1972.

Hay et al., "Autoxidation Reactions Catalyzed by Cobalt Acetate Bromide", Canadian Journal of Chemistry, vol. 43, pp. 1306-1317, 1965.

Li et al., "Oxidation of Alkynes By Cobalt Acetate Bromide: A New Mode of Action for an Important Industrial Catalyst", Journal of Molecular Catalysis A: Chemical 145, pp. 111-120, 1999.

Maki et al., "Antidiabetic Drugs to Benzoquinone and Naphthoquinone Dyes", Ullmann's Encyclopedia of Industrial Chemistry, vol. A3, pp. 555-569, 1985.

Kamiya, "The Autoxication of Tetralin Catalysed by Cobalt Salt and Sodium Bromide in Acetic Acid", vol. 22, pp. 2029-2038, 1966.

W. Partenheimer, "Methodology and Scope of Metal/Bromide Autoxidation of Hydrocarbons", Catalysis Today, vol. 23, pp. 69-158, 1995.

Landau et al., "Development of the M-C Process", Scope, vol. 64, No. 10, pp. 20-26, Oct. 1968.

Partenheimer, "Characterization of the Reaction of Cobalt (II) Acetate, Dioxygen and Acetic Acid, and Its Significance in Autoxidation Reactions", Journal of Molecular Catalysis, pp. 35-46, 1991.

Iwahama et al, "Production of Hydrogen Peroxide via Aerobic Oxidation of Alcohols Catalyzed by N-Hydroxyphthalimide", Organic Process Research & Development, vol. 4, No. 2, pp. 94-97, 2000.

Suresh et al., "Engineering Aspects of Industrial Liquid-Phase Air Oxidation of Hydrocarbons", Ind. Eng. Chem. Res., vol. 39, pp. 3958-3997, 2000.

Shiraishi et al., "Selective Synthesis of 2,6-naphthalenedicarboxylic Acid by Use of Cyclodextrin as Catalyst", Journal of Molecular Catalysis A. Chemical, vol. 139, pp. 149-158, 1999, (Abstract).

Szymansks-Buzar et al., "Activation of Hydrocarbon Molecules via Co(III)-RH Interaction in Trifluoroacetic Acid Solution", Journal of Molecular Catalysis, vol. 5, pp. 341-348, 1979.

Metelski et al., "Mechanistic Role of Benzylic Bromides in the Catalytic Autoxidation of Methylarenes", Articles, vol. 29, pp. 2434-2439, 2000.

Jiao et al., "Kinetics of Manganese (III) Acetate in Acetic Acid: Generation of Mn(III) With Co(III), Ce(IV), and Dibromide Radicals; Reactions of Mn(III) With Mn(II), Co (II), Hydrogen Bromide and Alkali Bromides", Inorg. Chem., vol. 29, pp. 1549-1554, 2000.

Paartenheimer et al., "Nature of the Co-Mn-Br Catalyst in the Methylaromatic Compounds Process", Catalytic Selective Oxidation, Chapter 7, pp. 81-88, 1992.

Chester et al., "Zirconium Cocatalysis of the Cobalt-Catalyzed Autoxidation of Alkylaromatic Hydrocarbons", Journal of Catalysis, vol. 46, pp. 308-319, 1977.

Rogovin et al, "Silicate Xerogels Containing Cobalt as Heterogeneous Catalysts for the Side-Chain Oxidation of Alkyl Aromatic Compounds With Tert-Butyl Hydroperoxide", Journal of Molecular Catalysis A: Chemical, vol. 138, pp. 315-318, 1999.

Chavan et al., "Formation and role of Cobalt and Maganese cluster Complexes in the Oxidation of p-Xylene", Journal of Molecular Catalysis: A Chemical, vol. 161, pp. 49-64, 2000.

Graham H. Jones, "A Mechanistic Study of the Origins of Synergy and Antagonism in the Cobalt Acetate Bromide and Manganese Acetate Bromide Catalysed Autoxidation of p-Xylene", Imperial Chemical Industries Ltd., Paper E/15/82. pp. 2137-2163, Jan. 26, 1982.

Bryant et al., "Mobil's Process for TPA", Chemical Engineering Progress, vol. 67, No. 9, pp. 69-75, 1971.

Graham H. Jones, "p-Xylene Autoxidation Studies, Oxidation of Cobalt (II) and Manganese (II) Acetates by Peracids", J.C.S. Chemistry Com., pp. 536-537, 1979.

Kamiya et al., "The Autoxidation of Aromatic Hydrocarbons Catalyzed with Cobaltic Acetate in Acetic Acid Solution", Journal of Catalysis, vol. 25, pp. 326-333, 1972.

Scott et al., "Kinetics of the Cobalt-Catalyzed Autoxidation of Toluene in Acetic Acid", The Journal of Physical Chemistry, vol. 76, No. 11, pp. 1520-1524, 1972.

RA Sheldon, "Liquid Phase Autoxidation", Catalytic Oxidation, pp. 150-175, 1995.

Kataliz et al., "Kinetics and Catalysis", Russian Origianal, vol. 19, No. 4, Part 2, Jul.-Aug. 1978.

International Search Report Mailed on Jul. 15, 2003.

International Search Report dated Nov. 18, 2005.

* cited by examiner

METHOD OF MAKING HALOPHTHALIC ACIDS AND HALOPHTHALIC ANHYDRIDES

This application is a Continuation in Part of U.S. patent application Ser. No. 10/882,762, entitled "METHOD OF MAKING HALOPHTHALIC ACIDS AND HALOPHTHALIC ANHYDRIDES" filed on Jun. 30, 2004 now abandoned, which is herein incorporated by reference.

BACKGROUND OF THE INVENTION

This invention relates to a method of preparing substituted aromatic carboxylic acid compounds. In particular, the present invention relates to liquid phase reaction of halogen-substituted ortho-xylene to produce halophthalic acid and halophthalic anhydride.

Oxidation of dialkyl benzenes has long been used to produce dicarboxylic acids. The oxidation has also been carried out in liquid phase in presence of a solvent. Of particular interest has been the oxidation of dimethyl benzene (xylene) to phthalic acid and the oxidation of para-xylene to terephthalic acid, which is in turn employed in the production of polybutylene terephthalate. Various methods for oxidizing ortho-xylene are known. For example, U.S. Pat. No. 3,402,184 describes oxidation of ortho-xylene in acetic acid solvent in the presence of a bromine promoter. U.S. Pat. Nos. 5,958,821; 5,981,420; and 6,020,522 describe oxidation of ortho-xylene in acetic acid solvent in the presence of a hydroxyimide promoter. Methods for preparing 4-chlorophthalic anhydride are also known. However, these methods typically involve aromatization of a Diels-Alder adduct of chloroprene and a maleic anhydride as in U.S. Pat. No. 5,322,954, or chlorination of phthalic acid as in Japanese patent applications 07258152 and 02129143. The chlorination process may also produce highly undesirable polychlorinated biphenyls. There is a need for a method for producing 4-chlorophthalic anhydride which does not involve handling toxic chloroprene or chlorine gas.

The liquid phase oxidation of xylene to phthalic acid requires the use of a catalyst, typically a cobalt/manganese/bromide catalyst system, and is generally performed in a carboxylic acid solvent such as acetic acid. The catalyst system may be augmented by the use of a co-catalyst such as zirconium, hafnium or cerium. Phthalic acid is an easily isolable solid, which can be filtered out of the reaction mixture.

Liquid phase oxidation, using a cobalt/manganese/bromide catalyst system and a carboxylic acid solvent, has also been applied to halogenated xylene with some success. The oxidation of the halogenated xylene is, however, more difficult than the oxidation of xylene due to presence of a halogen, which is an electron withdrawing substituent, on the benzene ring. The greater difficulty in oxidation results in a lower reaction selectivity and a larger amount of partial oxidation and side products than seen in the liquid phase oxidation of xylene under similar conditions. Additionally, the relatively soluble halogenated phthalic acid is difficult to separate from the partial oxidation and side products. Thus it is clear that in order for a method of halogenated xylene liquid phase oxidation to be successful, the reaction yield and the reaction selectivity must be very high and by-product formation should be minimized. Furthermore, in order to improve the commercial attractiveness of the liquid phase oxidation of halogenated xylene, effective methods for recovering high purity acetic acid (ex., up to 99.9 weight percent purity and having less than 0.01 weight percent of HCl) for reuse in the oxidation reaction are also desirable.

BRIEF SUMMARY OF THE INVENTION

In one aspect, the present invention provides a method of preparing a halophthalic acid I

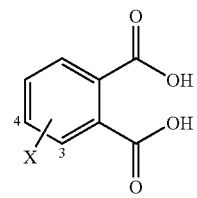

wherein X is a fluorine, chlorine, bromine, or iodine atom; said method comprising the steps of contacting in a liquid phase reaction mixture at least one halogen-substituted ortho-xylene with oxygen and acetic acid at a temperature in a range between about 120° C. and about 220° C. in the presence of a catalyst system. The catalyst system consists essentially of a source of cobalt ions, a source of manganese ions, and a source of bromide ions. The reaction mixture is characterized by an initial molar ratio of cobalt ion to halogen-substituted ortho-xylene of less than about 2%, an initial molar ratio of manganese ion to halogen-substituted ortho-xylene of less than about 1.5%, and an initial molar ratio of bromide ion to halogen-substituted ortho-xylene of less than about 0.5%. The oxygen is present in an amount corresponding to a partial pressure of oxygen in a range between about 0.00001 and about 15 bar. The product mixture comprises less than 10 percent halogen-substituted ortho-xylene starting material and a halophthalic acid product. In addition, the product mixture contains less than about 10,000 parts per million (ppm) halobenzoic acid by-product and less than about 1000 parts per million (ppm) halophthalide by-product based on a total amount of halophthalic acid present in the product mixture.

In another aspect, the present invention relates to a method of preparing a halophthalic anhydride comprising less than about less than about 500 parts per million halobenzoic acid by-product and less than about 500 parts per million halophthalide by-product.

In yet another aspect, the present invention provides a method of preparing a halophthalic acid wherein the acetic acid employed during one or more steps of the process is recovered for reuse. The method comprises the steps of: Step (A) contacting in a liquid phase reaction mixture at least one halogen-substituted ortho-xylene with oxygen and acetic acid at a temperature in a range between about 120° C. and about 220° C. in the presence of a catalyst system to provide a first product mixture comprising less than 10 percent halogen-substituted ortho-xylene starting material, a halophthalic acid product, and less than about 10,000 parts per million halobenzoic acid by-product, and less than about 1000 parts per million halophthalide based on a total amount of halophthalic acid present in the first product mixture; and Step (B) stripping a mixture comprising water, acetic acid, and hydrochloric acid from the first product mixture; to afford the crude halophthalic acid and a crude recovered acetic acid solvent comprising water, acetic acid, and hydrochloric acid.

The catalyst system employed in Step (A) consists essentially of a source of cobalt, ion, a source of manganese ions, and a source of bromide ions. The reaction mixture of Step (A) is characterized by an initial molar ratio of cobalt ion to halogen-substituted ortho-xylene of less than about 2%, an initial molar ratio of manganese ion to halogen-substituted ortho-xylene of less than about 1.5%, and an initial molar ratio of bromide ion to halogen-substituted ortho-xylene of less than about 0.5%. The oxygen is present in the reaction mixture in an amount corresponding to a partial pressure of oxygen in a range between about 0.0001 and about 15 bar.

In a further aspect of the invention, distillation techniques are provided for recovering purified acetic acid from the crude recovered acetic acid solvent.

DETAILED DESCRIPTION OF THE INVENTION

Figure 1:
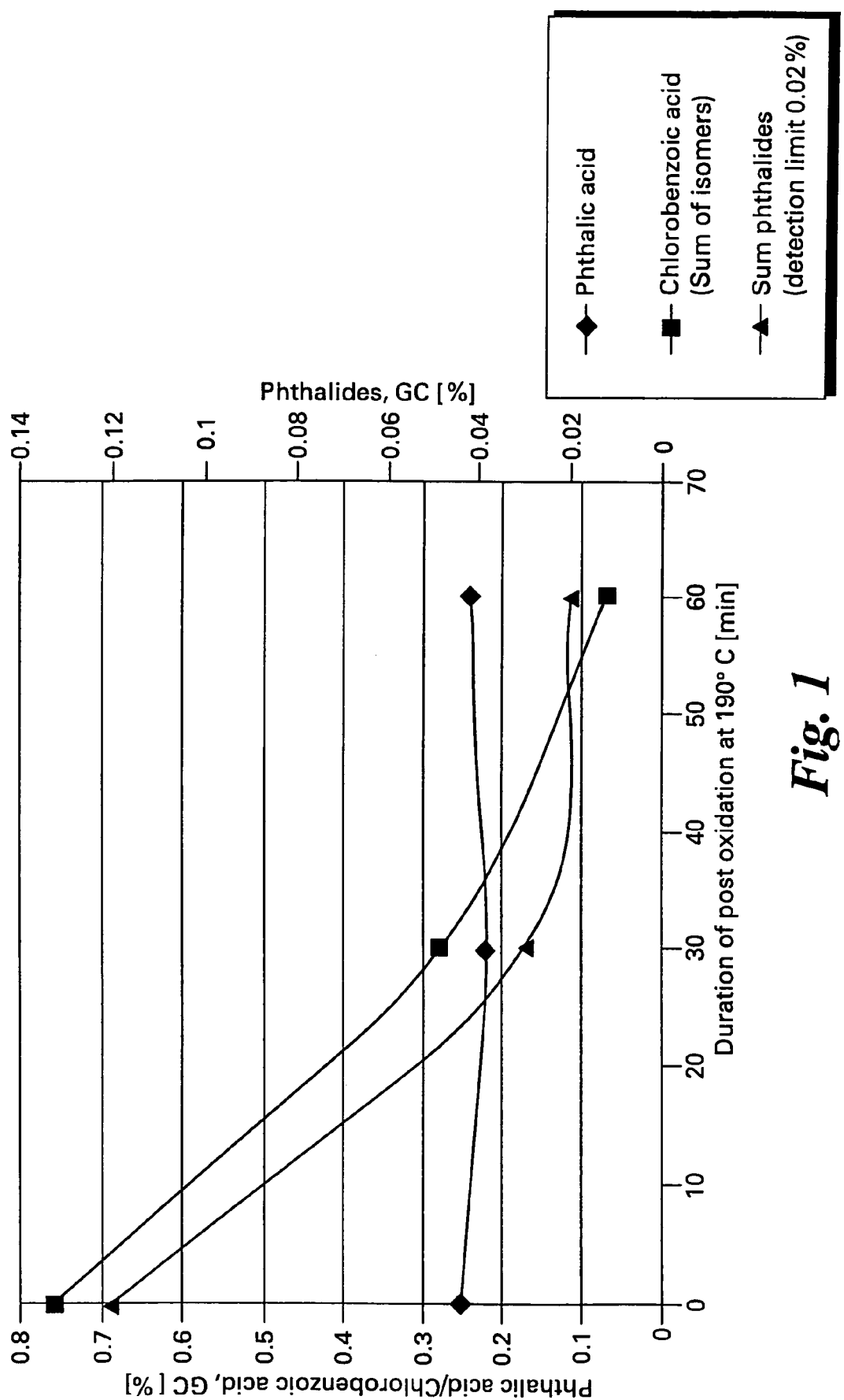
FIG. 1 shows the Influence of post-oxidation duration on by-product formation during oxidation of chloro-o-xylene under standard conditions.

The present invention may be understood more readily by reference to the following detailed description of preferred embodiments of the invention and the examples included herein. In this specification and in the claims which follow, reference will be made to a number of terms which shall be defined to have the following meanings.

The singular forms "a", "an" and "the" include plural referents unless the context clearly dictates otherwise.

"Optional" or "optionally" means that the subsequently described event or circumstance may or may not occur, and that the description includes instances where the event occurs and instances where it does not.

"Ortho-xylene" used herein is also known as 1,2-dimethylbenzene.

As used herein the term "aromatic radical" refers to a radical having a valence of at least one and comprising at least one aromatic ring. Examples of aromatic radicals include phenyl, pyridyl, furanyl, thienyl, naphthyl, phenylene, and biphenyl. The term includes groups containing both aromatic and aliphatic components, for example a benzyl group, a phenethyl group or a naphthylmethyl group. The term also includes groups comprising both aromatic and cycloaliphatic groups for example 4-cyclopropylphenyl and 1,2,3,4-tetrahydronaphthalen-1-yl.

As used herein the term "aliphatic radical" refers to a radical having a valence of at least one and consisting of a linear or branched array of atoms which is not cyclic. The array may include heteroatoms such as nitrogen, sulfur and oxygen or may be composed exclusively of carbon and hydrogen. Examples of aliphatic radicals include methyl, methylene, ethyl, ethylene, hexyl, hexamethylene and the like.

As used herein the term "cycloaliphatic radical" refers to a radical having a valance of at least one and comprising an array of atoms which is cyclic but which is not aromatic, and which does not further comprise an aromatic ring. The array may include heteroatoms such as nitrogen, sulfur and oxygen or may be composed exclusively of carbon and hydrogen. Examples of cycloaliphatic radicals include cyclopropyl, cyclopentyl cyclohexyl, 2-cyclohexylethy-1-yl, tetrahydrofuranyl and the like.

As, noted, the present invention relates to a method of preparing substituted aromatic carboxylic acid compounds. In particular, the present invention relates to liquid phase reaction of halogen-substituted ortho-xylene to produce a halophthalic acid which may be converted to a halophthalic anhydride.

In one embodiment said at least one halogen-substituted ortho-xylene is a monohalo-ortho-xylene. The halogen substituent may be in the 3 position (the 3-isomer) or in the 4 position (the 4-isomer). The halogen-substituted ortho-xylene used may also be a mixture of the 3-isomer and the 4-isomer. The halogen may be selected from fluorine, chlorine, bromine, or iodine. In one particular embodiment the halogen-substituted ortho-xylene is a 4-halo ortho-xylene, for example 4-fluoro- or 4-chloro-ortho-xylene. In another embodiment the halogen-substituted ortho-xylene is a mixture comprising 4-halo- and 3-halo-ortho-xylenes, for example a mixture of 4-fluoro- and 3-fluoro-ortho- xylene. In another particular embodiment the halogen-substituted ortho-xylene is a mixture of 4-chloro-ortho-xylene (also known as 4-chloro-1,2-dimethylbenzene) and 3-chloro-ortho-xylene (also known as 3-chloro-1,2-dimethylbenzene). In one embodiment the mixture of 4-chloro-1,2-dimethylbenzene and 3-chloro-1,2-dimethylbenzene comprises at least about 95 mole percent of 3-chloro-1,2-dimethylbenzene. In another embodiment the mixture of 4-chloro-1,2-dimethylbenzene and 3-chloro-1,2-dimethylbenzene comprises at least about 95 mole percent of 4-chloro-1,2-dimethylbenzene. In yet another embodiment the halogen-substituted ortho-xylene consists essentially of 4-chloro-1,2-dimethylbenzene. When 3-halo-ortho-xylene is present, it comprises in some embodiments about 0.001-35 molar percent, in other embodiments about 0.001-15 molar percent, in other embodiments about 0.01-12 molar percent, and in still other embodiments about 0.1-10 molar percent of total halogen-substituted ortho-xylene substrate undergoing oxidation.

According to the method of the present invention a halogen-substituted ortho-xylene is converted to a halogen-substituted phthalic acid by contacting in a liquid phase the halogen-substituted ortho-xylene in the presence of at least one solvent, which in some embodiments comprises a lower aliphatic carboxylic acid. Illustrative examples of lower aliphatic carboxylic acids employed in the present invention, include, but are not limited to, acetic acid, propionic acid, butanoic acid, pentanoic acid, or hexanoic acid. In one embodiment the lower aliphatic carboxylic acid is acetic acid. In some instances anhydrous acetic acid may be employed. Alternatively a mixture of acetic acid and water may be employed. In one embodiment the acetic acid may contain up to about 3 percent by weight water. Typically the acetic acid is present in an amount of about 7 to about 3 parts by weight to 1 part by weight of halo-substituted ortho-xylene. Preferably the acetic acid is present in an amount of about 5 to about 3 parts by weight to 1 part by weight of halogen-substituted ortho-xylene. The solvent may be recovered and reused following the reaction. For example, in some embodiments the product mixture is stripped to dryness to remove essentially all volatile materials, including, but not limited to, solvent before further treatment.

The catalyst system consists essentially of a source of cobalt ion, a source of manganese ion and a source of bromide ion. Useful cobalt, manganese, and bromine sources are those sources, which provide soluble forms of ionic cobalt, ionic manganese, and ionic bromine. Cobalt, and manganese sources that may be used include the metals themselves or any of their salts, complexes or compounds, and organometallic compounds. These cobalt, and manganese sources include, but are not limited to, cobalt and manganese acetates, citrates, stearates, napthenates, acetylacetonates, benzoylacetonates, carbonates, sulfates, bromides, chlorides, fluorides, nitrates, hydroxides, alkoxides, nitrides, triflates, hydrates of the foregoing, and mixtures of the foregoing.

In one embodiment of the present invention the source of cobalt ions is at least one cobalt containing species selected from the group consisting of metallic cobalt, salts of cobalt, complexes and organometallic compounds containing cobalt. In one embodiment the cobalt in the cobalt source is in a +2 or +3 oxidation state. In one embodiment the source of cobalt ions is at least one species selected from the group consisting of cobalt sulfate, cobalt bromide, cobalt chloride, cobalt fluoride, cobalt iodide, cobalt nitrate, cobalt stearate, cobalt carbonate, cobalt naphthalate, cobalt (II) hydroxide, cobalt (II) phosphate, cobalt (III) fluoride, cobaltous acetate, cobalt(II) acetylacetonate, cobalt (II) benzoylacetonate, cobalt(III) acetylacetonate, and cobalt(II) hexafluoroacetylacetonate, and combinations thereof.

In some embodiments the source of manganese ions is at least one manganese containing species selected from the group consisting of metallic manganese, salts of manganese, complexes and organometallic compounds containing manganese. In one embodiment of the present invention the source of manganese ions is a manganese compound in a +2 or +3 oxidation state. Suitable sources of manganese ions include manganese (II) fluoride, manganese (II) chloride, manganese (II) bromide, manganese (II) iodide, manganese (III) fluoride, manganese (II) acetate, manganese sulfate, manganese nitrate, manganese carbonate, manganese (III) acetate, manganese(II) acetylacetonate, manganese(III) acetylacetonate, manganese (II) hexafluoroacetylacetonate, and manganese (III) hexafluoroacetylacetonate, and combinations thereof.

The source of bromide ions is at least one bromine-containing species selected from the group consisting of inorganic bromide salts, organic bromide salts, inorganic bromine compounds comprising covalently bound bromine (e.g. BrCl), organic bromine compounds comprising covalently bound bromine, and elemental bromine. Suitable sources of bromide ion include alkali metal bromides, alkaline earth metal bromides, lanthanide metal bromides, transition metal bromides, quaternary ammonium bromides, quaternary phosphonium bromides, tetrabromosilane, acetyl bromide, oxalyl bromide, carbonyl dibromide, and tertiary-butyl bromide. Additional examples of inorganic bromide ion sources include bromine and hydrogen bromide. Additional examples of organic organic bromide ion sources include tetrabromoethane, ethyl bromide, ethylene bromide, bromoform, xylyl bromide, xylylene bromide and mixtures thereof may be employed as a source of bromide ions.

The amounts of the various catalyst system components are conveniently expressed in terms of mole percent (mol %) of the cobalt, manganese, and bromine ions present and are based on the amount of halogen-substituted ortho-xylene present at the beginning of the reaction. Typically the cobalt source is generally present in amount corresponding to about 0.25 to about 2 mole percent cobalt ion relative to the halogen-substituted ortho-xylene at the outset of the reaction. In another embodiment the cobalt source is present in amount corresponding to about 0.5 to about 1.5 mole percent cobalt ion relative to the halogen-substituted ortho-xylene at the outset of the reaction. In yet another embodiment the cobalt source is present in amount corresponding to about 1 to about 1.5 mole percent cobalt ion relative to the halogen-substituted ortho-xylene at the outset of the reaction.

The manganese source is present in an amount corresponding to about 0.25 mole percent to about 1.5 mole percent manganese ion relative to the amount of halogen-substituted ortho-xylene at the outset of the reaction. In one embodiment the manganese source is present in an amount corresponding to about 0.5 mole percent to about 1.25 mole percent manganese ion relative to the amount of halogen-substituted ortho-xylene at the outset of the reaction. In another embodiment the manganese source is present in an amount corresponding to about 0.6 mole percent to about 1.0 mole percent manganese ion relative to the amount of halogen-substituted ortho-xylene at the outset of the reaction.

The bromide source is present in an amount corresponding to about 0.005 mole percent to about 0.5 mole percent relative to the amount of halogen-substituted ortho-xylene at the outset of the reaction. In one embodiment of the present invention the amount of the bromine source is present in an amount corresponding to about 0.05 mole percent to about 0.5 mole percent relative to the amount of halogen-substituted ortho-xylene at the outset of the reaction. In yet another embodiment, the bromide source is present in an amount corresponding to about 0.15 mole percent to about 0.35 mole percent relative to the amount of halogen-substituted ortho-xylene at the outset of the reaction. It has been discovered that in liquid phase oxidations employing halogen-substituted ortho-xylene the amount of bromide can have a significant impact on the amount of impurities present in the final product. It has been discovered that the use of decreasing molar percentages of bromide results in a product, either halophthalic acid or anhydride, with a decreased level of impurities such as halophthalide and halobenzoic acids. Lower levels of bromide, such as molar percentages less than about 0.35, may be useful in producing high purity halophthalic acid or anhydride in even very large scale liquid phase oxidations such as those employing thousands of kilograms of halogen-substituted ortho-xylene.

Suitable molecular oxygen containing gases include gases or combinations of gases which are a source of molecular oxygen ($O_2$), for example, 100 percent oxygen and mixtures of oxygen with one or more inert gases wherein the concentration of oxygen is sufficient to effect oxidation under the reaction conditions. The oxygen source used in the present invention may be high purity oxygen molecular oxygen, air, oxygen-enriched air, or oxygen diluted with another gas which has no negative effects on the reaction, such as nitrogen, and noble gases such as helium and argon. In one embodiment of the present invention the diluent gas is nitrogen. The concentration of diluent gas, when present, in the oxygen source is typically in a range between about 1 to about 95 volume percent, preferably about 10 to about 80 volume percent. In one embodiment the oxygen source is oxygen-enriched air containing about 28 mole percent oxygen. As will be appreciated by one of skill in the art, the concentration of oxygen may affect the rate of the reaction.

Oxygen in the form of an oxygen source may be introduced into the reaction mixture by any convenient means. In one embodiment the reaction mixture is agitated or stirred under a positive pressure of the oxygen source, for example a positive pressure of an oxygen-nitrogen gas mixture. In one embodiment of the present invention oxygen is present during the oxidation reaction in an amount corresponding to a partial pressure of oxygen in a range between about 0.00001 and about 15 bar. Alternatively the oxygen is present in an amount corresponding to a partial pressure of oxygen in a range between about 0.001 and about 10 bar. In yet another embodiment the oxygen is present in an amount corresponding to a partial pressure of oxygen in a range between about 0.01 and about 1 bar.

In an exemplary process, the halophthalic acid may be produced by contacting the halogen-substituted ortho-xylene with oxygen, the cobalt source, the manganese source and the bromide source in a solution in acetic acid in a pressurized reaction vessel. The contacting is carried out at a temperature effective to promote oxidation of at least one and preferably both methyl groups of the halogen-substituted ortho-xylene in the presence of the catalyst and oxygen source. Preferably the reaction mixture is heated to a temperature in a range between about 80° C. and either the temperature at which either catalyst or promoter is no longer effective for promoting reaction or the effective boiling point of the reaction mixture under the prevailing pressure, whichever of the two is the lower temperature. The temperature of the reaction is typically about 120° C. to about 220° C. More preferably the reaction mixture is heated to a temperature in a range of between about 150° C. and about 190° C. The contacting is carried out at a pressure of in a range between about 10 and about 30 bar, preferably in a range between about 18 and about 25 bar.

Typically the molecular oxygen containing gas is introduced throughout the course of the oxidation reaction. In one embodiment the molecular oxygen containing gas is introduced to the reaction mixture and the flow of the molecular oxygen containing gas is maintained at a rate that creates an oxygen containing off gas with an oxygen concentration of less than about 6 percent by volume, preferably less than about 4 percent by volume. The off gas oxygen concentration may be determined by paramagnetic oxygen transduction analysis or other method known in the art. Useful flow rates are typically greater than or equal to 0.5 normal cubic meter ($m^3$)/hour per kilogram (kg) of halogen-substituted ortho-xylene and preferably greater than or equal to 1.0 normal cubic meter ($m^3$)/hour per kilogram (kg) of halogen-substituted ortho-xylene. A normal cubic meter is defined as cubic meter under standard temperature and pressure condition. Preferably the reaction mixture is agitated using standard methods such as mechanical stirring. The flow of the molecular oxygen containing gas continues until the off gas oxygen concentration exceeds about 4 percent by volume, indicating a slowing of the reaction. Once the off gas oxygen concentration exceeds about 4 percent by volume the flow of the molecular oxygen containing gas is modified so as to maintain the off gas oxygen concentration below about 5 percent by volume and the temperature of the reaction may be increased. It is preferable, however, for the temperature to remain below about 200° C. The flow of the molecular oxygen containing gas may be modified in several ways. The molecular oxygen containing gas may be diluted with an inert gas so as to decrease the oxygen concentration in the molecular oxygen containing gas, the flow rate of the molecular oxygen containing gas may be decreased, the source of the molecular oxygen containing gas may be changed so as to employ a molecular oxygen containing gas with a lower oxygen concentration or these methods may be combined so as to maintain the off gas oxygen concentration below about 5 percent by volume. The modified flow of molecular oxygen containing gas is continued until at least about 90 percent of halogen-substituted ortho-xylene has been converted to halophthalic acid, preferably until greater than 95 percent has been converted. The amount of conversion achieved in the reaction can readily be determined through the use of gas chromatography, mass spectrometry, or other methods known in the art such as high performance liquid chromatography (HPLC).

After the reaction reaches the desired level of conversion, the halophthalic acid may be recovered as a product mixture comprising halophthalic acid I and halophthalic anhydride II

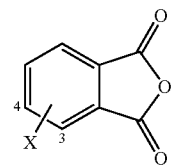

wherein X is a fluorine, chlorine, bromine, or iodine atom. Halophthalic acid and halophthalic anhydride with a high degree of purity are required for various applications. Such high degree of purity may be achieved by the method described herein. By-products produced include the isomeric halobenzoic acids III, and the isomeric halophthalides IV

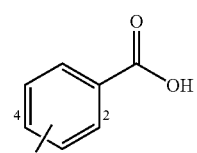

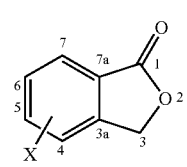

wherein X is a fluorine, chlorine, bromine, or iodine atom. It should be noted that there are 3 possible isomeric forms of halobenzoic acids III: (i) X in the "2" position, (ii) X in the "3" position, and (iii) X in the "4" position. There are 4 such isomers possible for halophthalides IV: (i) X in the "4" position, (ii) X in the "5" position, (iii) X in the "6" position, and (iv) X in the "7" position. In one embodiment of the present invention, halophthalic acid and halophthalic anhydride products prepared by the method of the present invention contain less than about 1000 parts per million of halophthalide (all halophthalide isomers), preferably less than about 600 parts per million of halophthalide, and more preferably less than about 500 parts per million of halophthalide. Additionally, halophthalic acid and halophthalic anhydride containing less than about 1 percent by weight of phthalic anhydride (the product of dehalogenation) may also be achieved. In another embodiment of the present invention the product mixture comprises less than about 10,000 parts per million of halobenzoic acid based on a total amount of halophthalic acid present in the initially formed product mixture. In yet another embodiment the initially formed product mixture comprises less than about 8,000 parts per million of halobenzoic acid. In a preferred embodiment of the present invention the initially formed product mixture comprises less than about 5,000 parts per million of halobenzoic acid.

In one embodiment of the present invention the method of preparing a halophthalic acid comprises oxidation products resulting from oxidation of at least one of and sometimes both the two ortho-methyl groups of the halogen-substituted ortho-xylene. In various embodiments the oxidation products comprise at least one of a substituted or unsubstituted ortho-benzene dicarboxylic acid (also known as phthalic acid), or a substituted or unsubstituted aromatic anhydride derived from the corresponding ortho-benzenedicarboxylic acid (also known as phthalic anhydride). In one embodiment the oxidation products comprise at least one of phthalic acid, phthalic anhydride, halotoluic acid, halophthalic acid, halophthalic anhydride, or mixtures thereof. In still another embodiment the oxidation products comprise at least one of phthalic acid, phthalic anhydride, chlorotoluic acid, 3-chlorophthalic acid, 3-chlorophthalic anhydride, 4-chlorophthalic acid, 4-chlorophthalic anhydride, or mixtures thereof. It is understood that product mixtures initially comprising halophthalic acid may be dehydrated to form a product mixture comprising in some embodiments up to 100 mole percent (based on halophthalic acid) of halophthalic anhydride. It is also understood that product mixtures initially comprising halophthalic anhydride may be hydrated to form a product mixture comprising in some embodiments up to 100 mole percent (based on halophthalic anhydride) of halophthalic acid. In a particular embodiment the initially formed oxidation product comprises chlorotoluic acid, 4-chlorophthalic acid, and 4-chlorophthalic anhydride. In another particular embodiment the initially formed oxidation product comprises isomeric chlorotoluic acids and a mixture of 3-chloro- and 4-chlorophthalic acid, and 3-chloro- and 4-chlorophthalic anhydride. When ortho-xylene is present as a contaminant in the halogen-substituted ortho-xylene undergoing oxidation, then phthalic acid phthalic anhydride, and/or toluic acid may be present in the initially formed oxidation product.

In one aspect the present invention provides a method of preparing a halophthalic anhydride. A first reaction mixture is formed by contacting in a liquid phase reaction mixture at least one halogen-substituted ortho-xylene with oxygen and acetic acid at a temperature in a range between about 120° C. and about 220° C. in the presence of a catalyst system, consisting essentially of a source of cobalt, ion, a source of manganese ions, and a source of bromide ions, said reaction mixture being characterized by an initial molar ratio of cobalt ion to halogen-substituted ortho-xylene of less than about 2%, an initial molar ratio of manganese ion to halogen-substituted ortho-xylene of less than about 1.5%, and an initial molar ratio of bromide ion to halogen-substituted ortho-xylene of less than about 0.5%, said oxygen being present in an amount corresponding to a partial pressure of oxygen in a range between about 0.0001 and about 15 bar. Following the oxidation reaction, a first product mixture is obtained which comprises less than about 10 percent of the total amount of halogen-substituted ortho-xylene starting material (i.e., conversion>90%) less than about 10,000 parts per million halobenzoic acid and less than about 1000 parts per million halophthalide based on a total amount of halophthalic acid present in the product mixture. In another embodiment the first product mixture comprises less than about 5 percent halogen-substituted ortho-xylene starting material and less than about 10,000 parts per million halobenzoic acid and less than about 1000 parts per million halophthalide based on a total amount of halophthalic acid present in the product mixture. In yet another embodiment the first product mixture comprises less than about 10 percent halogen-substituted ortho-xylene starting material and less than about 5,000 parts per million halobenzoic acid and less than about 500 parts per million halophthalide based on a total amount of halophthalic acid present in the product mixture. In a preferred embodiment of the present invention the first product mixture comprises less than about 5 percent halogen-substituted ortho-xylene starting material and less than about 5,000 parts per million halobenzoic acid and less than about 500 parts per million halophthalide based on a total amount of halophthalic acid present in the product mixture. In an alternate preferred embodiment of the present invention the first product mixture comprises less than about 2 percent halogen-substituted ortho-xylene starting material and less than about 5000 parts per million of halobenzoic acid and less than about 500 parts per million halophthalide based on a total amount of halophthalic acid present in the product mixture.

The conversion of the product halophthalic acid to halophthalic anhydride can effected by stripping water and acetic acid from the first product mixture and effecting ring closure of the halophthalic acid. The stripping of water and acetic acid from the first product mixture is carried out at ambient pressure temperature in the range of between about 100° C. and about 120° C. Alternatively, the stripping of water and acetic acid can be carried out at sub-atmospheric pressure. In one embodiment a stripping regime includes stripping at both atmospheric and sub-atmospheric pressure.

The first product mixture typically comprises the product halophthalic acid, by-product halobenzoic acids, by-product halophthides, and residual catalyst mixture. In one embodiment of the present invention the first product mixture is subjected to conditions which effect ring closure of the product halophthalic acid to afford a second product mixture comprising halophthalic anhydride, the halobenzoic acids, the halophthalides and the residual catalyst mixture.

In one embodiment of the present invention a first "evaporative separation" is performed on the second product mixture in order to separate the product halophthalic anhydride from residual catalyst mixture. The term "evaporative separation" includes such techniques as distillation, thin film evaporation, sublimation and vacuum transfer, and generally refers to a process in which volatile components of a product mixture are separated from non-volatile components in the product mixture. Typically, vacuum distillation or thin film evaporation is preferred. This first evaporative separation typically affords a distillate ( the "third product mixture") comprising a purified halophthalic anhydride and a residual catalyst mixture comprising halophthalic anhydride, halobenzoic acids, halophthalides, and components of the catalyst system employed. In yet another embodiment a second "evaporative separation" of the purified halophthalic anhydride (the third product mixture) is carried out to afford a halophthalic anhydride comprising less than about 1000 parts per million of a halobenzoic acid and less than about 500 parts per million halophthalide. In a preferred embodiment of the present invention the halophthalic anhydride obtained from the second evaporative separation comprises less than about 500 parts per million of halobenzoic acid and less than about 100 parts per million halophthalide.

The residual catalyst mixture may be recovered and reused in oxidation reactions of the type disclosed by the present invention. Such recycling of the catalyst system affords a variety of economic and environmental benefits. In one embodiment of the present invention the residual catalyst mixture is used as an additional source of cobalt ions, manganese ions, and bromide ions for the oxidation of a halo-substituted ortho-xylene starting material.

Most of the acetic acid as well as water produced in the oxidation reaction can be removed by distillation. The acetic acid and water are removed as a vapor and condensed. The water may then be removed from the acetic acid and the acetic acid may be recycled. Some dehydration of the halophthalic acid to form halophthalic anhydride may occur simultaneously with the removal of acetic acid and water. Furthermore, the removal of acetic acid and water may be combined with dehydration of the halophthalic acid in a single step. Dehydration is typically carried out thermally by distillation under vacuum at an elevated temperature. Dehydration may also be carried out by other chemical reactions well known to those skilled in the art such as treatment with acetic anhydride. After distillation, the purity of the halophthalic anhydride is typically greater than about 95 percent, preferably greater than about 97 percent, and most preferably greater than about 99 percent as measured by gas chromatography.

In one aspect the present invention provides a method for the preparation of a polyetherimide comprising structural units derived from the halophthalic anhydride provided by the present invention. Methods for the preparation polyetherimides comprising structural units derived from a halophthalic anhydride are known in the art, for example, U.S. Pat. Nos. 5,917,005 and 6,020,456 which are incorporated herein by reference in their entirety. Thus in one aspect, the halophthalic anhydride comprising 4-halophthalic anhydride provided by the present invention is reacted with a diamine such a m-phenylene diamine to provide a bisimide comprising structure V. Polyetherimides may be synthesized by the reaction of the bis(halophthalimide) V

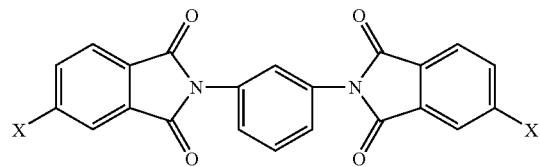

V wherein X is halogen, with an alkali metal salt of a dihydroxy substituted aromatic compound in the presence or absence of phase transfer catalyst. Suitable phase transfer catalysts are disclosed in U.S. Pat. No. 5,229,482, which is herein incorporated by reference. Suitable dihydroxy substituted aromatic hydrocarbons include those having the formula (VI)

HO-A$^1$-OH    (VI)

wherein A$^1$ is a divalent aromatic hydrocarbon radical. Suitable A$^1$ radicals include m-phenylene, p-phenylene, 4,4'-biphenylene, 4,4'-bi(3,5-dimethyl)phenylene, 2,3-bis(4-phenylene)propane and similar radicals such as those disclosed by name or formula in U.S. Pat. No. 4,217,438. Bisphenol VI includes bisphenol A (BPA), bisphenol M, bisphenol Z and the like.

The A$^1$ radical preferably has the formula (VII)

-A$^2$-Q-A$^3$-    (VII)

wherein each of A$^2$ and A$^3$ is a monocyclic divalent aromatic hydrocarbon radical and Q is a bridging hydrocarbon radical in which one or two atoms separate A$^2$ from A$^3$. The free valence bonds in formula (VII) are usually in the meta or para positions of A$^2$ and A$^3$ in relation to Q. A$^2$ and A$^3$ may be substituted phenylene or hydrocarbon-substituted derivative thereof, illustrative substituents (one or more) being alkyl and alkenyl, unsubstituted phenylene radicals are preferred. Both A$^2$ and A$^3$ are preferably p-phenylene, although both may be o- or m-phenylene or one o- or m-phenylene and the other p-phenylene.

The bridging radical, Q, is one in which one or two atoms, preferably one, separate A$^2$ from A$^3$. Illustrative radicals of this type are methylene, cyclohexylmethylene, 2-(2,2,1)-bicycloheptylmethylene, ethylene, isopropylidene, neopentylidene, cyclohexylidene, and adamantylidene. The preferred radical of formula (IV) is 2,2-bis(4-phenylene)propane radical which is derived from bisphenol A and in which Q is isopropylidene and A$^2$ and A$^3$ are each p-phenylene.

It is clear to one of ordinary skill in the art that any impurities present in the halophthalic anhydride will be carried through to subsequent steps in the polyetherimide synthesis. The presence of significant levels of impurities in subsequent steps can interfere with polymerization and cause discoloration of the final product, polyetherimide.

As noted, in one aspect the present invention provides a method for making a polyetherimide comprising structural units derived from a halophthalic anhydride, itself made by the method of the present invention. Thus, the method for making a polyetherimide comprises contacting in a liquid phase reaction mixture at least one halogen-substituted ortho-xylene with oxygen and acetic acid at a temperature in a range between about 120° C. and about 220° C. in the presence of a catalyst system. The catalyst system consists essentially of a source of cobalt ions, a source of manganese ions, and a source of bromide ions. The reaction mixture is characterized by an initial molar ratio of cobalt ion to halogen-substituted ortho-xylene of less than about 2%, an initial molar ratio of manganese ion to halogen-substituted ortho-xylene of less than about 1.5%, and an initial molar ratio of bromide ion to halogen-substituted ortho-xylene of less than about 0.5%. The oxygen is present in an amount corresponding to a partial pressure of oxygen in a range between about 0.00001 and about 15 bar. There is obtained a product mixture comprising less than 10 percent halogen-substituted ortho-xylene starting material, a halophthalic acid product, and less than about 10,000 parts per million halobenzoic acid by-product and less than 1000 parts per million halophthalide by-product based on a total amount of halophthalic acid present in the product mixture. The product halophthalic acid is then dehydrated to form a halophthalic anhydride which is typically purified by distillation prior to its condensation reaction with a diamine such as 1,3-diaminobenzene to form bis(halophthalimide) V wherein X is a halogen; and subsequently reacting bis(halophthalimide) (V) with an alkali metal salt of a dihydroxy substituted aromatic compound having the formula (VI) wherein A$^1$ is a divalent aromatic radical to form a polyetherimide.

In one embodiment the present invention provides a polyetherimide comprising structural units derived from 4-chlorophthalic anhydride, m-phenylene diamine and bisphenol A.

The first product mixture comprises water, acetic acid, and hydrochloric acid. This product mixture can be further processed to recover acetic acid, which can be used in the oxidation process. In other embodiments, the first product mixture may comprise water and acetic acid; or water, acetic acid, hydrochloric acid, and methyl acetate. The presence of hydrogen chloride is believed to be due to dehalogenation of one or more of the starting materials (e.g., chloro o-xylene), the intermediates (e.g. 4-chloro-2-methylbenzoic acid), the product (e.g. 4-chlorophthalic acid), and by-products (e.g., 4-chlorophthalide) used in or formed during the oxidation reaction of chloro o-xylene to chlorophthalic acid. Those skilled in the art will understand that the use of starting materials other than chloro o-xylene, for example bromo o-xylene, will produce hydrogen bromide via analogous dehydrohalogenation processes. Typically, the HCl concentration in the vapor phase of the oxidation reaction medium is under 2000 ppm. In one embodiment, upon completion of the oxidation reaction, the first product mixture can be stripped to afford a crude chlorophthalic acid product and recovered acetic acid solvent, which comprises water, acetic acid, and hydrochloric acid.

The crude recovered acetic acid solvent can be further purified by at least one distillation step to afford purified acetic acid. The crude recovered acetic acid solvent may be present as a component in a multicomponent mixture, for example a 2-component, 3-component, 4-component, or 5-component mixture. The crude recovered acetic acid solvent is sometimes referred to herein as a "feed stream" since it represents the material being fed to a solvent purification and recovery system. Non-limiting examples of 2-component, 3-component, 4-component, and 5-component feed-streams include acetic acid-water (2-component), acetic acid-water-HCl (3-component); and acetic acid-water-HCl-methyl acetate (4-component), and acetic acid-water-HCl-methyl acetate-methanol (5-component) mixtures, respectively. The feed-stream may comprise acetic acid in any amount from greater than or equal to about 50 weight percent to 99 weight percent. In one embodiment, multi-component feed-stream comprises at least 50 weight percent of acetic acid, less than about 4 weight percent HCl, and less than about 20 weight percent of methyl acetate. In another embodiment; a multi-component feed stream comprises at least 65 weight percent of acetic acid, less than about 3.8 weight percent of HCl, and less than about 5 weight percent of methyl acetate. In yet another embodiment, a multi-component feed stream comprises at least 82 weight percent of acetic acid, less than about 0.3 weight percent of HCl, and less than about 2.5 weight percent of methyl acetate. In each of the aforesaid embodiments, the multi-component feed stream may further comprise additional components such as water, chlorophthalic acids, chlorobenzoic acids, and bromide salts.

In one embodiment of the present invention the distillation step comprises introducing a mixture comprising water, acetic acid, and hydrochloric acid into a vertical distillation column, said column having a top outlet adapted for the removal of an "overheads" (distillate) stream, a bottom outlet adapted for removing a "bottoms" (reboiler) stream, and a "side-draw" outlet adapted for removing a "side" stream. In one embodiment of the present invention, the "overheads" stream is "water-rich", the "bottoms" stream is "acetic acid-rich" and the "side" stream" is "HCl-rich". A water-rich overhead stream is defined herein as a mixture comprising greater than or equal to about 80 weight percent water. In an embodiment, the water rich component comprises greater than or equal to about 80 weight percent of water, less than or equal to about 20 weight percent of acetic acid, and 0-500 ppm of HCl. When the feed stream further comprises methyl acetate and methanol (in addition to acetic acid, water and HCl), separation of the stream in a distillation column having a top outlet adapted for the removal of an "overheads" stream, a bottom outlet adapted for removing a "bottoms" stream, and a "side-draw" outlet adapted for removing a "side" stream, the overheads stream is water rich comprising, in one embodiment, between about 70 and about 100 weight percent of water, between 0 to about 1 weight percent of methanol, and between 0 and about 30 weight percent of methyl acetate, and in another embodiment between about 85 and about 100 weight percent of water, between 0 to about 1 weight percent of methanol, and between 0 and about 15 weight percent of methyl acetate.

An HCl-rich side-draw stream is herein defined as a mixture comprising from about 0.1-5 weight percent HCl, relative to the total weight of the side-draw stream, water in an amount corresponding to between about 25 and about 35 percent by weight of the total weight of the side-draw stream, and acetic acid in an amount corresponding to between about 65 and about 75 percent by weight of the total weight of the side-draw stream. In certain instances, the composition of the HCl-rich stream may correspond to that of a HCl-acetic acid-water azeotrope, which typically has around 3.5 weight percent of HCl.

The acetic acid-rich bottoms stream is herein defined as a mixture comprising at least 90 weight percent of acetic acid. Typically, the bulk of the remainder of the bottoms stream is made up of water, although other components may at times be present. Purification of solvent mixtures comprising acetic acid, water, and HCl, and optionally other components such as methanol and methyl acetate may be performed on a laboratory-scale using an Oldershaw-type distillation column comprising a top outlet adapted for the removal of an overheads stream, a bottom outlet adapted for removing a bottoms stream, and a side-draw outlet adapted for removing a side-draw stream. Such distillation columns are available commercially from Normschliff Geratebau. The distillation column can be operated at sub-ambient, ambient, or super-ambient pressures. Operating pressure can be varied over a range from about 100-5200 millibars in an embodiment, from about 300-3100 millibars in another embodiment, and from about 800-1100 millibars in still another embodiment. The feed-stream is introduced into the column via a feed-port on the column in a manner so as to facilitate recovery of the product either as a bottom stream or a top stream (distillate). The section of the column above the feed-port is referred to as the rectification or enriching section, and the section of the column below the feed-port is referred to as the stripping section. In an embodiment, the undesired HCl is removed as the HCl-rich component as a side-draw above the feed-port, and in another embodiment, the water-rich component, comprising minor amounts of acetic acid, and methyl acetate and methanol (if present) is removed as a distillate at the top of the column. Acetic acid is removed as an acetic acid-rich component as the bottom stream (below the feed-port). The HCl content in the side-draw stream is generally about 1-3.5 weight percent, typically about 1.5-2.5 weight percent. The acetic acid content in the side-draw stream is generally about 65-80 weight percent. The acetic acid-rich component generally has a purity of at least 90 weight percent in an embodiment, greater than 95 weight percent in another embodiment, and greater than or equal to about 98 weight percent in yet another embodiment. In various embodiments, it is possible to recover at least 75 weight percent, at least 85 weight percent, and at least 95 weight percent of high purity acetic acid, relative to the weight of acetic acid present in the crude recovered acetic acid solvent. It is frequently possible to recover acetic acid having purity between about 95 to 99.9 percent the using the distillation techniques described herein. The HCl content in the acetic acid-rich component is typically less than about 500 ppm in another embodiment, and less than 250 ppm in another embodiment.

EXAMPLES

The following examples are set forth to provide those of ordinary skill in the art with a detailed description of how the methods claimed herein are carried out and evaluated, and are not intended to limit the scope of what the inventors regard as their invention. Unless indicated otherwise, parts are by weight, temperature is in ° C. In Tables 1 and 2, values given for analytical measurements are bracketed ( ) when measured by HPLC. Otherwise values were determined using gas chromatography.

Oxidation Halo Ortho Xylenes to Halophthatlic Acids

Laboratory scale reactions were carried out in a 3.5 liter, pressurized Hastelloy C22 reaction vessel adapted for heating and cooling, and equipped with a mechanical agitator, a gas inlet valve attached to a subsurface gas inlet tube, an internal thermocouple, a pressure transducer, and a gas outlet valve linked to a condenser and receiving vessel operated at atmospheric pressure. The chloro-o-xylene starting material was typically a mixture of 3-chloro and 4-chloro isomers. The 3-, 4-isomer ratio was determined by $^1$H-NMR and gas chromatography (GC). Acetic acid was employed as the reaction solvent. The catalyst system typically consisted of cobaltous acetate, manganous acetate and sodium bromide and was charged to the reaction vessel under ambient conditions as a 15-16% solution in acetic acid. In some instances sodium acetate was added as an anticorrosive agent. After the reactants had been charged, the reaction vessel was sealed and the vessel was placed in a test cell, pressurized with nitrogen to about 19 bar and heated to the initial reaction temperature, typically about 160° C. while stirring the reaction mixture at about 800 rpm. Compressed air was then introduced as the source of oxygen at a rate such that the concentration of oxygen in the effluent gas emerging from the gas outlet valve was less than about 2%, typically about 0.5-1.0%. Initially, the flow of air was relatively modest, but then was increased such that the oxygen level in the effluent gas was maintained in the range of about 0.1 to about 1.0%. An exotherm was observed as the reaction initiated and appropriate cooling was employed to maintain a temperature of 160° C. After about 60 minutes, the set-point temperature was increased to 175° C. The rate of addition of the additional compressed air was regulated such that the concentration of oxygen in the gas emerging from the reactor at the gas outlet valve comprised less than about 1%. When most of the chloro-o-xylene had been consumed, it was observed that the amount of oxygen present in the gas emerging from the reactor at the gas outlet valve rose rapidly. This rapid rise in oxygen concentration in the gas stream emerging from the gas outlet valve was referred to as "oxygen breakthrough" and indicated that the reaction had entered a "post-oxidation" phase in which the bulk of the starting chloro-o-xylene had been consumed. In this post-oxidation phase of the reaction, a phase characterized by the high conversion (>90%) of starting material to products and decreasing reaction rate, the compressed air employed as the stoichiometric oxidant was further diluted with nitrogen such that the gas stream exiting the reactor at the gas outlet valve contained less than about 4% oxygen. Typically, the temperature of the reaction mixture was raised to about 190° C. at the outset of the post-oxidation phase and was maintained at that temperature for a period of from about 0.5 to about 3 hours. The total amount of oxygen fed to the reactor was typically 110-130% of that required for stoichiometric reaction (3 mol of $O_2$/mol of chloroxylene). Upon completion of the reaction, the homogeneous reaction mixture was assayed by high performance liquid chromatography (HPLC) and gas chromatography (GC). Typically, conversion of starting chloro-o-xylene to product chlorophthalic acid was substantially in excess of 90% and the concentration of chlorobenzoic acid by-product was less than about 10,000 ppm and the concentration of halophthalide by-product was less than about 1000 ppm based on the total amount of halophthalic acid present in the product mixture.

Example 1

A 3.5 liter reaction vessel equipped as described above was charged with a 95:5 mixture of 4-chloro-o-xylene and 3-chloro-o-xylene (492.1g, 3.50 mol), acetic acid (1925 mL, 32.06 mol), cobaltous acetate tetrahydrate (13.1 g, 0.0526 mol, 1.50 mole % based on 3.5 moles of 3- and 4-chloro-o-xylene), manganous acetate tetrahydrate (6.4g, 0.0261 mol, 0.75 mole % based on 3.5 moles of 3- and 4-chloro-o-xylene), sodium bromide (0.6g, 0.0060 mol, 0.17 mole % based on 3.5 moles of 3- and 4-chloro-o-xylene), and sodium acetate (2.9 g, 0.0354 mol, 1.01 mole % based on 3.5 moles of 3- and 4-chloro-o-xylene). The reaction vessel was sealed and pressurized with nitrogen to 19 bar and then heated to about 160° C. Compressed air was then introduced into the reaction mixture at a rate such that the concentration of oxygen in the gas emerging from the reactor gas outlet valve was about 0.5%. The reaction temperature was maintained at about 160° C. for 1 hour and was then raised to about 175° C. and was maintained at that temperature until "oxygen breakthrough" was noted. Oxygen breakthrough marked the beginning of the post-oxidation phase of the reaction. The compressed air being fed to the reactor was then diluted with sufficient nitrogen to limit the concentration of oxygen in the gas emerging from the reactor gas outlet valve to less than about 2%. The reaction temperature was raised to about 190° C. and maintained at that temperature throughout the post-oxidation phase which lasted approximately three hours. The reaction mixture was then assayed by BPLC and GC and found to contain the product diacids as a mixture of 3-chlorophthalic acid and 4-chlrorophthalic acid containing less than 10,000 ppm chlorobenzoic acids. Conversion of starting material to products was in excess of 90 percent.

Examples 2-14

Data for a series of oxidation reactions conducted as described in Example 1 together with modifications to reaction parameters indicated are gathered in Table 1. The data demonstrate the effectiveness of the method of the present invention to produce high yields of chlorophthalic acid while limiting the amount of chlorobenzoic acid by-products. In Table 1 the header "Variation" refers to the reaction parameter being varied in the Example, "standard" refers to the amounts of reagents and reaction conditions used in Example 2 which are given below.

Conditions of Example 2:

(A) Reagents

| | |
|---|---|
| 492.1 g (3.5 Mol) | 3-/4-Chloro-1,2-dimethylbenzene (95% 4-isomer + 5% 3-isomer) |
| 1925 g | acetic acid |
| 13.1 g (52.5 mMol) | Cobaltous acetate tetrahydrate |
| 6.4 g (26.25 mMol) | Manganous acetate, tetrahydrate |
| 0.65 g (6.3 mMol) | sodium bromide |
| 12.3 g (150.0 mMol) | sodium acetate (anhydrous) |

(B) Oxidation Conditions 19 bar$_{abs}$ nitrogen pressure, stirrer speed 800 rpm. Temperature 152° C. at initial oxygen introduction. Cooling begun immediately upon reaction initiation to maintain an internal temperature of about 160° C. After 60 min the temperature was raised to 175° C. At the beginning of the post-oxidation phase of the reaction the temperature was raised to 190° C. for a period of 60 minutes.

| | |
|---|---|
| Induction period: | <1 min |
| Reaction time: | 144 min + 60 min post reaction at 190° C. |
| Reaction Temp.: | first 160–161° C., then 173–177° C., end 190° C. |
| Pressure: | 19 bar$_{abs}$ |
| Gas flow rates: | initial 1050 l/h (scaled value 210 l/h), much slower at "EOR". |

Still referring to Table 1, the term "air input" refers to the variation in which the reaction was "oxygen limited" meaning that the gas flow rate was initially 900 l/h (scaled value 180 l/h), much slower at the end of the reaction ("EOR"). The heading "Oxidation Conds." refers to the conditions employed in the oxidation reaction which were either (1) the "standard" conditions as given for Example 2 or the "oxygen limited" reaction conditions of Examples 4 and 5. The heading "Post-Oxidation Conds." refers to the duration (time) and temperature of the reaction following "oxygen breakthrough". The heading "Cl-phthalic acid" refers to the total amount of 3- and 4-chlorophthalic acid present in the crude product mixture at the end of the oxidation reaction. The values given in the column headed "Cl-phthalic acid" are the combined "area percent" of the peaks attributed to 3- and 4-chlorophthalic acid in a gas chromatogram of the crude product mixture. The heading "Isomeric ClBA's" refers to the total amount of 2-, 3-, and 4-chlorobenzoic acids present in the crude reaction mixture and expressed in parts per million (ppm). 2-chlorobenzoic acid, 3-chlorobenzoic acid, and 4-chlorobenzoic acid are believed to arise by decarboxylation of 3-chlorophthalic acid and 4-chlorophthalic acid.

Conversion of Halophthalic Acids to Halophthalic Anhydrides

Example 2a

Cyclization Procedure Using Acetic Anhydride

The crude reaction product of Example 2 was divided into two identical fractions each weighing 1355 grams. One of the two fractions was subjected to distillation at atmospheric pressure (pot temperature 150° C.) until a total of about 952.9 grams of a mixture of water and acetic acid had been collected in the receiving vessel. The maximum head temperature was 122° C. When the head temperature reached 122° C. acetic anhydride (196.5 g, 1.93 mole) was added dropwise to the distillation flask and the resultant blue solution (no precipitate was observed) was heated at reflux (136° C.) for a two hour period. A mixture of acetic acid and acetic anhydride (198.6 grams) was then distilled off at atmospheric pressure (pot temperature 160° C.). Thereafter, vacuum was carefully applied to remove any remaining acetic anhydride, and the product chlorophthalic anhydride was distilled under vacuum. Two fractions were collected, the first distilled at 70-98° C. at a pressure in a range between 18 and 645 mbar. The first fraction (81.2 grams) contained residual acetic acid, acetic anhydride and product chlorophthalic anhydride. The second fraction distilled at between 136 and 144° C. at a pressure in a range between 3 and 5 mbar. The second fraction consisted essentially of a mixture of 3- and 4-chlorophthalic

TABLE 1

OXIDATION OF CHLOROXYLENE TO CHLOROPHTHALIC ACID

| Example | Trial-No. | Variation | Oxidation-Conds. | Post-Oxidation | Cl-phthalic acid[a] | Isomeric ClBA's |
|---|---|---|---|---|---|---|
| 2 | 128a | Standard | Standard | 60 min/190° C. | 97.6% | (1334) |
| 3 | 130a | Standard | Standard | 60 min/190° C. | 97.0–98.5 | (0961) |
| 4 | 131a | air-input | O2-limited | 60 min/190° C. | 97.6 | (1371) |
| 5 | 135a | 0.22 Mol % Br | O2-limited | None | 97.0–98.5 | (0837) |
| 6 | 136a | 0.22 Mol % Br | Standard | 60 min/190° C. | 97.0–98.5 | (0843) |
| 7 | 137a | 150% Catalyst | Standard | 60 min/190° C. | 97.0–98.5 | (0941) |
| 8 | 138a | Postoxidation time 30 min | Standard | 30 min/190° C. | 97.0–98.5 | (0897) |
| 9 | 148a | 50% Catalyst | Standard | 60 min/190° C. | 97.0–98.5 | (0926) |
| 10 | 149a | 0.14 Mol % Br | Standard | 60 min/190° C. | 97.0–98.5 | (1261) |
| 11 | 150a | low NaOAc-level | Standard | 60 min/190° C. | 97.0–98.5 | (1244) |
| 12 | 152a | 10% less Mn | Standard | 60 min/190° C. | 97.0–98.5 | (1185) |
| 13 | 153a | Standard | Standard | 60 min/190° C. | 97.0–98.5 | (1536) |
| 14 | 154a | low NaQAc-level | Standard | 60 min/190° C. | 97.0–98.5 | (1435) |

[a]% of peak total peak area (HPLC) attributed to halophthalic acids, halobenzoic acids and halophthalides. All values fell in a range between 97.0 and 98.5%.

anhydride (276.6 g, 1.52 mole, 86.6% of theory). Examples 3a-14a were carried out as described for Example 2. Data are gathered in Table 2.

Example 14b

Thermal Cyclization Procedure

The crude reaction product of Example 14 was sampled for analysis and then divided into two identical fractions (fractions "a" and "b") each weighing 1351 grams. Fraction "b" was charged to a 2-liter flask. Distillation was carried out at atmospheric pressure (maximum pot temperature 175° C.) until a total of about 1012.8 grams of distillate had been removed. Vacuum was then carefully applied until a pressure of about 80 mbar was achieved and the mixture was heated under vacuum for about 3 hours at 175° C. to effect ring closure and water removal. The crude anhydride was vacuum distilled to afford purified chlorophthalic anhydride (282.6 g, 88.5%) as a colorless solid.

TABLE 2

CONVERSION OF HALOPHTHALIC ACID TO HALOPHTHALIC ANHYDRIDE

| Example | Trial-No. | % Yield ClPA | [5-ClP][a] | [4-ClP][b] | [PA][c] | [ClBA][d] |
|---|---|---|---|---|---|---|
| 2a | 128a | 86.6 | <100 (18) | <100 | 2300 | 100/400 |
| 3a | 130a | 84.8 | <100 | <100 | 2400 | 1200 |
| 3b | 130b | 63 | <100 | <100 | 2500 | 3900 |
| 4 | 131a | 89.6 | <100 (29) | <100 | 2500 | 900 (91) |
| 5 | 135a | 86.4 | 1100 | 100 | 2500 | 7600 |
| 6 | 136a | 87.4 | <100 (19) | <100 | 2300 | 2900 (184) |
| 7 | 137a | 83.2 | <100 (15) | <100 | 2200 | 8800 (126) |
| 8 | 138a | 88.5 | 200 (119) | <100 | 2200 | 2800 (167) |
| 9 | 148a | 85.8 | <100 (20) | <100 | 2200 | 2500 (219) |
| 10a | 149a | 81.4 | <100 (19) | <100 | 2500 | 3400 (210) |
| 11a | 150a | 88.3 | <100 (16) | <100 | 2600 | 4200 (111) |
| 11b | 150b | 87.2 | <100 (16) | <100 | 2500 | 3400 |
| 12a | 152a | 89.5 | <100 (20) | <100 | 2200 | 3600 (203) |
| 12b | 152b | — | <100 (23) | <100 | 2400 | 3100 |
| 13a | 153a | 88.4 | <100 (21) | <100 | 2300 | 2200 (194) |
| 14a | 154a | 88.9 | <100 (18) | <100 | 2900 | 6100 (214) |
| 14b | 154b | 88.5 | — | — | — | — |

[a]5-chlorophthalide (ppm)
[b]4-chlorophthalide (ppm)
[c]phthalic acid (ppm)
[d]total isomeric chlorobenzoic acids (ppm)

Figure 2:
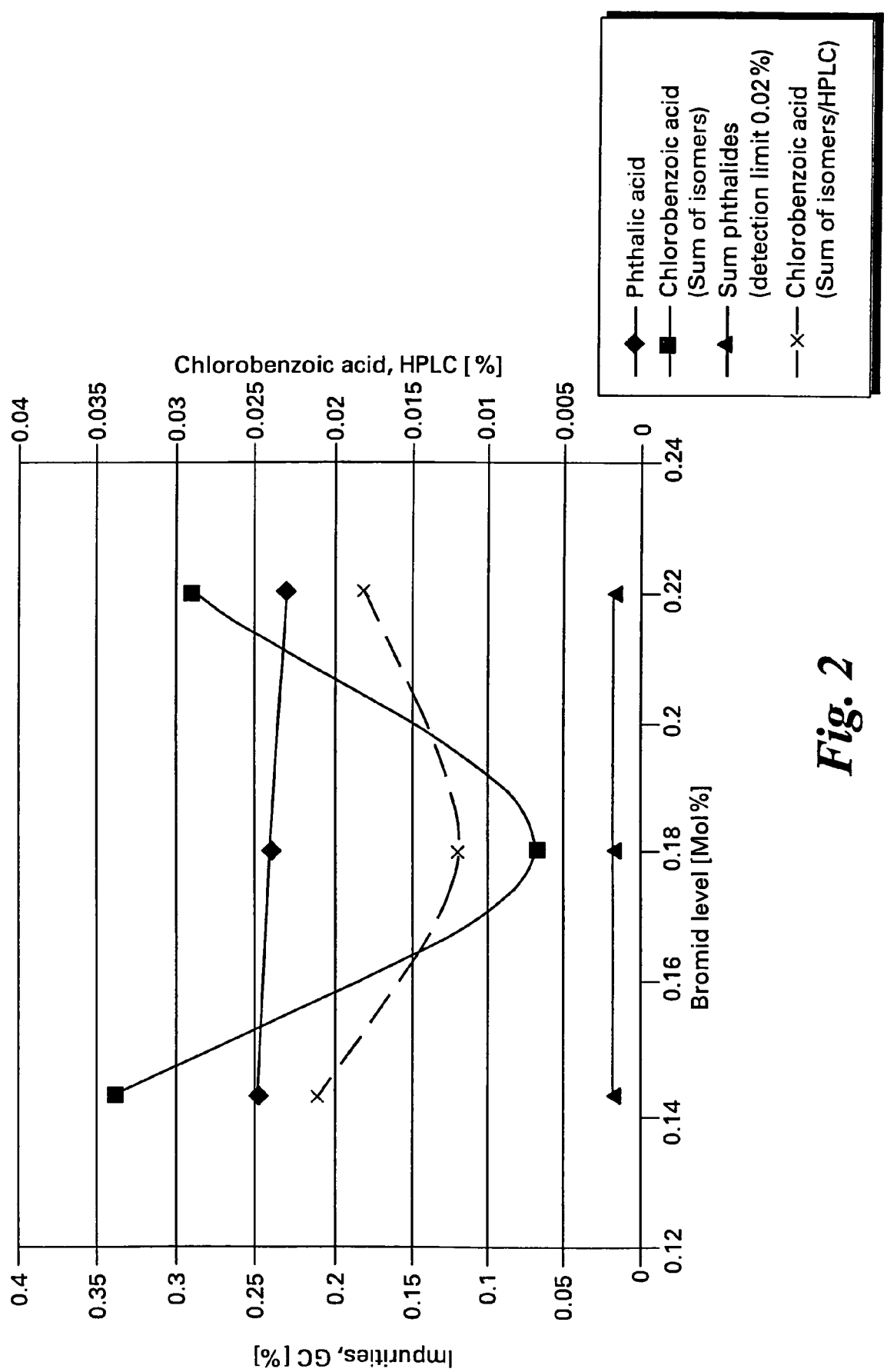
FIG. 2 shows the influence of bromide level on formation of by-products during oxidation of chloro-o-xylene under standard conditions.
Figure 3:
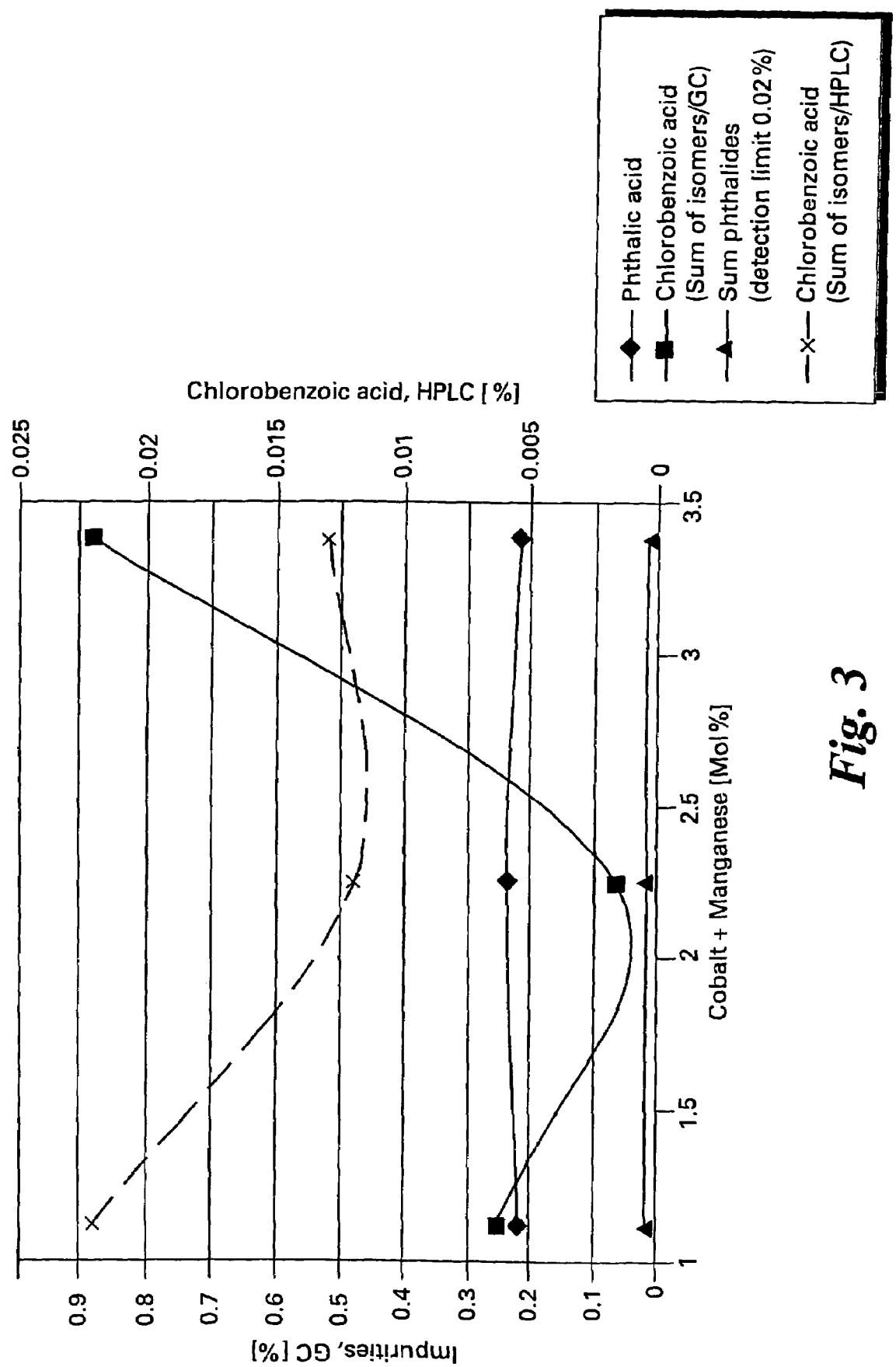
FIG. 3 shows the influence of catalyst level on formation of by-products during oxidation of chloro-o-xylene.

The data provided in Tables 1 and 2 clearly demonstrate the surprising efficacy of the method of the instant invention. FIGS. 1-3 were prepared using data from experiments carried out during the studies comprising the instant invention. FIG. 1 shows the effect of the post-oxidation conditions on the yields of product and by-products formed in the oxidation reaction. The data show that lower levels of chlorophthalides are obtained at post-oxidation times of 30 minutes or longer at 190° C. FIG. 2 illustrates the surprising influence of bromide level on the reaction outcome. Unexpectedly, for the oxidation of chloro-ortho-xylene under "standard" conditions, a bromide level in a range between about 0.14 and about 0.22 mole percent (relative to the initial amount of chloro-ortho-xylene) provides much lower levels of impurities. FIG. 3 illustrates the surprising influence of the catalyst concentration on the level of impurities found in the reaction product. FIG. 3 shows that higher levels of undesired chlorobenzoic acid impurities are formed when the catalyst level (combined "Co" and "Mn") exceeds about 3 mole percent.

Example 15

General Procedure for the Recovery of Acetic Acid

Acetic acid purification was carried out using a laboratory Oldershaw type distillation column having a total of 62 stages, which included a 60 plate perforated plate column, a reboiler and a condenser. The column had a silver vacuum jacket, an inner diameter of 30 mm, 80 holes per plate, an operating hold-up of 2 ml/plate, a hold-up volume of 0.15 ml/plate, and a column plate efficiency of 66%. The reboiler had a capacity of 6 liters with a 1000 Watt heater, controllable to desired power input. Reflux ratio was controlled on a time basis with an electromagnetically-controlled column head in conjunction with electronic controllers. Water was used as coolant for the condenser. The distillation set-up also included probes for measuring temperature at the column top and reboiler, probes for measuring the pressure in the reboiler and the pressure drop across the column; as well as provisions for pre-heating the feed-stream and sampling the streams emanating from the column. The distillation column was configured to have 5 ports, ports 1, 2, 3, 4, and 5, corresponding to stages 9, 17, 25, 39, 47, and 55, respectively. Stage 1 refers to the top tray, and stage 62 refers to the bottom tray. Peristaltic pumps were used to pump the feed and bottom streams. A pump was used to withdraw the side-draw stream. Mass flow rates were measured gravimetrically using electronic weighing balances. The column was operated under ambient pressure using the range of operating parameters shown in Table 3.

TABLE 3

| Operating Parameter | Value |
|---|---|
| Feed-stream pump rate (gm/hour) | 80–110 |
| Side-draw withdrawal rate (gm/hour) | 5–7.5 |
| Bottom stream withdrawal rate (gm/hour) | 65–90 |
| Heat (i/p) in Watts | 160–180 |
| Reflux ratio | 6–7.5 |
| Overhead stream take-off rate (gm/hour) | 5–17.5 |
| Pressure drop (millibar) | 65–75 |
| Pressure at reboiler (millibar) | 950–980 |
| Overhead temperature (° C.) | 80–100 |
| Bottom temperature (° C.) | 116–120 |

Comparative Example 1

In this Example, no side-draw was used in the distillation. A reflux ratio of 6 was used. The compositions of the fractions sampled at the various stages are shown in Table 4. The weight percent of water, which made up the remainder of each samples is not shown.

TABLE 4

| | Composition (Weight percent) | |
|---|---|---|
| Stage Number | Acetic acid | HCl |
| Distillate | 58.9 | 0.43 |
| 9 | 69.8 | 3.71 |
| 17 | 68.9 | 3.78 |
| 25 | 69.4 | 3.77 |
| 39 | 70.3 | 3.67 |

TABLE 4-continued

| Stage Number | Composition (Weight percent) | |
| --- | --- | --- |
| | Acetic acid | HCl |
| Feed (47) | 84.1 | 0.24 |
| 55 | 85.7 | 1.43 |
| Reboiler (62) | 89.0 | 0.20 |

Example 16

A reflux ration of 6 and a side draw from stage 25 of the distillation column was employed. The compositions of the fractions sampled at the various stages are shown in Table 5. The weight percent of water, which made up the remainder of each samples is not shown.

TABLE 5

| Stage Number | Composition (Weight percent) | |
| --- | --- | --- |
| | Acetic acid | HCl |
| Distillate | 15.7 | <0.01 |
| 9 | 23.9 | 0.00 |
| 17 | 45.6 | 0.02 |
| Side draw (25) | 70.7 | 2.26 |
| 39 | 70.3 | 2.82 |
| Feed (47) | 85.2 | 0.15 |
| 55 | 91.1 | 0.07 |
| Reboiler (62) | 99.2 | <0.01 |

Example 17

A reflux ratio of 6 and a side draw from stage 39 of the distillation column was used. The compositions of the fractions sampled at the various stages are shown in Table 6. The weight percent of water, which made up the remainder of each samples is not shown.

TABLE 6

| Stage Number | Composition (Weight percent) | |
| --- | --- | --- |
| | Acetic acid | HCl |
| Distillate | 9.6 | <0.01 |
| 9 | 16.5 | <0.01 |
| 17 | 32.3 | <0.01 |
| 25 | 62.0 | 0.40 |
| Side draw (39) | 71.3 | 2.60 |
| Feed (47) | 83.5 | 0.20 |
| 55 | 98.4 | 0.05 |
| Reboiler (62) | 99.3 | <0.01 |

Example 18

A reflux ratio of 6 was used. The compositions of the fractions sampled at the various stages are shown in Table 7. The weight percent of water, which made up the remainder of each samples is not shown.

TABLE 7

| Stage Number | Composition (Weight Percent) | | | |
| --- | --- | --- | --- | --- |
| | Acetic acid | HCl | Methyl acetate | Methanol |
| Distillate | 12.0 | <0.01 | 17.01 | 0.29 |
| 9 | 27.6 | <0.01 | <0.3 | <0.06 |
| 17 | 56.7 | 0.23 | <0.3 | <0.06 |
| 25 | 69.2 | 3.02 | <0.3 | <0.06 |
| Side draw (39) | 73.0 | 2.37 | <0.3 | <0.06 |
| Feed (47) | 84.9 | 0.16 | 1.98 | <0.06 |
| 55 | >99.5 | <0.01 | <0.3 | <0.06 |
| Reboiler (62) | .99.8 | ,0.01 | ,0.3 | ,0.06 |

Example 19

A reflux ratio of 7.5 was used. The compositions of the fractions sampled at the various stages are shown in Table 8. The weight percent of water, which made up the remainder of each samples is not shown. "ND" stands for "not detected".

TABLE 8

| Stage Number | Composition (Weight Percent) | | | |
| --- | --- | --- | --- | --- |
| | Acetic | HCl | Methyl | Methanol |
| Distillate | 7.0 | <0.01 | 16.10 | 0.42 |
| 9 | 14.1 | <0.01 | ND | ND |
| 17 | 28.7 | <0.01 | ND | ND |
| 25 | 34.2 | 0.04 | ND | ND |
| Side draw (39) | 70.3 | 2.91 | ND | ND |
| Feed (47) | 85.0 | 0.16 | 1.85 | <0.06 |
| 55 | >99.5 | <0.01 | ND | ND |
| Reboiler (62) | >99.8 | <0.01 | ND | ND |

Examples 16-19 illustrate the utility of withdrawing the side-draw stream in order to recover high purity acetic acid containing less than 0.01 weight percent of hydrochloric acid from aqueous feed streams comprising acetic acid and aqueous HCl; and acetic acid, aqueous HCl, methyl acetate, and methanol.

The invention has been described in detail with particular reference to preferred embodiments thereof, but it will be understood by those skilled in the art that variations and modifications can be effected within the spirit and scope of the invention.

What is claimed is:

1. A method of preparing a halophthalic acid, said method comprising the steps of:
    contacting in a liquid phase reaction mixture at least one halogen-substituted ortho-xylene with oxygen and acetic acid at a temperature in a range between about 120° C. and about 220° C. in the presence of a catalyst system,
    said catalyst system consisting essentially of a source of cobalt ions, a source of manganese ions, and a source of bromide ions,
    said reaction mixture being characterized by an initial molar ratio of cobalt ion to halogen-substituted ortho-xylene of less than about 2%, an initial molar ratio of manganese ion to halogen-substituted ortho-xylene of less than about 1.5%, and an initial molar ratio of bromide ion to halogen-substituted ortho-xylene of less than about 0.5%,
    said oxygen being present in an amount corresponding to a partial pressure of oxygen in a range between about 0.00001 and about 15 bar, to provide a product mixture comprising less than 10 percent halogen-substituted ortho-xylene starting material, a halophthalic acid product, and less than about 10,000 parts per million halobenzoic acid by-product and less than 1000 parts per million halophthalide by-product based on a total amount of halophthalic acid present in the product mixture.

2. The method according to claim 1 wherein the product mixture comprises less than about 5,000 parts per million halobenzoic acid.

3. The method according to claim 2 wherein the product mixture comprises less than about 1,000 parts per million halobenzoic acid.

4. The method according to claim 1 wherein said contacting is carried out at a temperature in a range between about 150° C. and about 200° C.

5. The method according to claim 1 wherein said at least one halogen-substituted ortho-xylene is a mixture of 3-chloro-1,2-dimethylbenzene and 4-chloro-1,2-dimethylbenzene.

6. The method according to claim 5 wherein said mixture comprises about 95 mole percent 3-chloro-1,2-dimethylbenzene.

7. The method according to claim 5 wherein said mixture comprises about 95 mole percent 4-chloro-1,2-dimethylbenzene.

8. The method according to claim 1 wherein said at least one halogen-substituted ortho-xylene consists essentially of 4-chloro-1,2-dimethylbenzene.

9. The method according to claim 1 wherein said source of cobalt ions is at least one cobalt containing species selected from the group consisting of metallic cobalt, salts of cobalt, and organometallic compounds containing cobalt.

10. The method according to claim 1 wherein said source of cobalt ions is comprises at least one of cobalt sulfate, cobalt bromide, cobalt chloride, cobalt fluoride, cobalt iodide, cobalt nitrate, cobalt stearate, cobalt carbonate, cobalt naphthalate, Co(OH)2, cobalt phosphate, cobalt (DI) fluoride, cobaltous acetate, cobalt (II) acetylacetonate, cobalt (IT) benzoylacetonate, cobalt(m) acetylacetonate, and cobalt (IT) hexafluoroacetylacetonate.

11. The method according to claim 1 wherein said source of manganese ions is at least one manganese containing species selected from the group consisting of metallic manganese, salts of manganese, and organometallic compounds containing manganese.

12. The method according to claim 1 wherein said source of manganese ions comprises at least one of manganese (II) fluoride, manganese (II) chloride, manganese (II) bromide, manganese (II) iodide, manganese (III) fluoride, manganese (II) acetate, manganese sulfate, manganese nitrate, manganese carbonate, manganese (II) acetate, manganese (II) acetylacetonate, manganese (III) acetylacetonate, manganese (II) hexafluoroacetylacetonate, and manganese (III) hexafluoroacetylacetonate.

13. The method according to claim 1 wherein said source of bromide ions is at least one bromine-containing species selected from the group consisting of inorganic bromide salts, organic bromide salts, inorganic bromine compounds comprising covalently bound bromine, organic bromine compounds comprising covalently bound bromine, BrCl, and elemental bromine.

14. The method according to claim 1 wherein said source of bromide ions comprises at least one of alkali metal bromide, alkaline earth metal bromides, lanthanide metal bromide, transition metal bromides, quaternary ammonium bromides, quaternary phosphonium bromides, tetrabromosilane, acetyl bromide, oxalyl bromide, carbonyl dibromide, and tertiary-butyl bromide.

15. The method according to claim 1 wherein said source of cobalt is less than about 1.5 mole percent based on the halogen-substituted ortho-xylene.

16. The method according to claim 1 wherein said source of manganese is less than about 1.0 mole percent based on the halogen-substituted ortho-xylene.

17. The method according to claim 1 wherein said source of bromide is less than about 0.35 mole percent based on the halogen-substituted ortho-xylene.

18. The method according to claim 1 wherein the product mixture comprises less than about 5 percent of halogen-substituted ortho-xylene and less than 10,000 parts per million halobenzoic acid.

19. The method according to claim 1, wherein the method further comprises addition of at least one diluent gas.

20. The method according to claim 19, wherein said diluent gas comprises nitrogen.

21. The method according to claim 1, wherein the partial pressure of oxygen in a range between about 0.001 and about 10 bar.

22. The method according to claim 1, wherein the acetic acid is present in an amount of between about 3 and 7 parts by weight per 1 part of halosubstituted ortho-xylene.

23. A method of preparing a chlorophthalic acid, said method comprising the steps of:
contacting in a liquid phase reaction mixture at least one chloro-substituted ortho-xylene with oxygen and acetic acid at a temperature in a range between about 120° C. and about 220° C. in the presence of a catalyst system,
said catalyst system consisting essentially of a source of cobalt, ion, a source of manganese ions, and a source of bromide ions,
said reaction mixture being characterized by an initial molar ratio of cobalt (II) acetate to chloro-substituted ortho-xylene of less than about 2%, an initial molar ratio of manganese (II) acetate to chloro-substituted ortho-xylene of less than about 1.5%, and an initial molar ratio of sodium bromide to chloro-substituted ortho-xylene of less than about 0.5%,
said oxygen being present in an amount corresponding to a partial pressure of oxygen in a range between about 0.00001 and about 15 bar,
to provide a product mixture comprising less than 10 percent chloro-substituted ortho-xylene starting material, a chlorophthalic acid product, and less than about 10,000 parts per million chlorobenzoic acid by-product and less than about 1000 parts per million chlorophthalide based on a total amount of chlorophthalic acid present in the product mixture.

24. A method of preparing a halophthalic acid, said method comprising the steps of:
Step (A) contacting in a liquid phase reaction mixture at least one halogen-substituted ortho-xylene with oxygen and acetic acid at a temperature in a range between about 120° C. and about 220° C. in the presence of a catalyst system,
said catalyst system consisting essentially of a source of cobalt ion, a source of manganese ions, and a source of bromide ions,
said reaction mixture being characterized by an initial molar ratio of cobalt ion to halogen-substituted ortho-xylene of less than about 2%, an initial molar ratio of manganese ion to halogen-substituted ortho-xylene of less than about 1.5%, and an initial molar ratio of bromide ion to halogen-substituted ortho-xylene of less than about 0.5%, said oxygen being present in an amount corresponding to a partial pressure of oxygen in a range between about 0.0001 and about 15 bar, to provide a first product mixture comprising less than 10 percent halogen-substituted ortho-xylene starting material, a halophthalic acid product, and less than about 10,000 parts per million halobenzoic acid by-product and les than 1000 parts per million halophthalide based on a total amount of halophthalic acid present in the first product mixture; and Step (B) stripping a mixture comprising water, acetic acid, and hydrochloric acid from the first product mixture; to afford a crude recovered acetic acid solvent comprising water, acetic acid, and hydrochloric acid.

25. The method according to claim 24 wherein the crude recovered acetic acid solvent is purified by at least one distillation step.

26. The method according to claim 25 wherein said distillation step comprises introducing a mixture comprising water, acetic acid, and hydrochloric acid into a distillation column and removing from said column a water-rich component, an acetic acid-rich component and an HCl-rich component.

27. The method according to claim 26 wherein said water-rich component is removed as a overheads stream comprising between about 85 and about 100 percent by weight water, from 0 to about 1 percent by weight methanol, and from 0 to about 15 percent by weight methyl acetate.

28. The method according to claim 26 wherein said acetic acid-rich component is removed as a bottoms stream comprising between about 95 and about 99.9 percent by weight acetic acid.

29. The method according to claim 26 wherein said HCl-rich component is removed as a side-draw stream.

30. The method according to claim 29 wherein said HCl-rich component comprises hydrochloric acid in a an amount corresponding to between about 0.1 and about 5.0 percent by weight of the total weight of the side-draw stream, water in a an amount corresponding to between about 25 and about 35 percent by weight of the total weight of the side-draw stream, and acetic acid in a an amount corresponding to between about 65 and about 75 percent by weight of the total weight of the side-draw stream.

* * * * *